US012303376B2

(12) United States Patent
MacTaggart et al.

(10) Patent No.: US 12,303,376 B2
(45) Date of Patent: May 20, 2025

(54) BYPASS GRAFT

(71) Applicant: Board of Regents of the University of Nebraska, Lincoln, NE (US)

(72) Inventors: Jason N. MacTaggart, Omaha, NE (US); Alexey Kamenskiy, Omaha, NE (US); Kaspars Maleckis, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 752 days.

(21) Appl. No.: 17/282,564

(22) PCT Filed: Oct. 3, 2019

(86) PCT No.: PCT/US2019/054401
§ 371 (c)(1),
(2) Date: Apr. 2, 2021

(87) PCT Pub. No.: WO2020/072717
PCT Pub. Date: Apr. 9, 2020

(65) Prior Publication Data
US 2021/0338412 A1  Nov. 4, 2021

Related U.S. Application Data

(60) Provisional application No. 62/741,828, filed on Oct. 5, 2018.

(51) Int. Cl.
*A61F 2/06* (2013.01)
*A61L 31/06* (2006.01)
(Continued)

(52) U.S. Cl.
CPC .............. *A61F 2/064* (2013.01); *A61L 31/06* (2013.01); *B29C 53/56* (2013.01); *B29C 53/80* (2013.01);
(Continued)

(58) Field of Classification Search
CPC .............. A61F 2/064; A61F 2210/0057; A61F 2220/0008; A61F 2220/0075;
(Continued)

(56) References Cited

U.S. PATENT DOCUMENTS 4,552,707 A  11/1985  How
6,939,372 B2  9/2005  Dong
(Continued)

FOREIGN PATENT DOCUMENTS

KR  20090113318  10/2009
WO  WO 2005/084730  9/2005
(Continued)

OTHER PUBLICATIONS

Adam et al., "Bypass versus angioplasty in severe ischaemia of the leg (BASIL): multicentre, randomised controlled trial," Lancet., Dec. 2005, 366(9501):1925-34, 10 pages.
(Continued)

*Primary Examiner* — Suzette J Gherbi
(74) *Attorney, Agent, or Firm* — Fish & Richardson P.C.

(57) ABSTRACT

Elastomeric bypass grafts (EBG) described herein can be pre-stretched and are able to accommodate limb flexion-induced or organ-induced deformations without producing excessive tortuosity or stresses. In comparison to known grafts, EBGs demonstrate significantly less tortuosity when used for lower extremity repair during limb flexion, and improved flow patterns within the grafts. Longitudinally pre-stretched EBGs described herein improve hemodynamics and may produce better healing responses in the harsh mechanical environment of the lower limbs, compared to known grafts.

17 Claims, 12 Drawing Sheets

(51) Int. Cl.
    *B29C 53/56*     (2006.01)
    *B29C 53/80*     (2006.01)
    *B29K 71/00*     (2006.01)
    *B29L 31/00*     (2006.01)

(52) U.S. Cl.
    CPC ............... *A61F 2210/0057* (2013.01); *A61F 2220/0008* (2013.01); *A61F 2220/0075* (2013.01); *A61F 2230/0091* (2013.01); *A61F 2240/001* (2013.01); *B29K 2071/00* (2013.01); *B29L 2031/7532* (2013.01)

(58) Field of Classification Search
    CPC ....... A61F 2230/0091; A61F 2240/001; A61L 31/06; B29C 53/56; B29C 53/80; B29K 2071/00; B29L 2031/7532
    See application file for complete search history.

(56) References Cited

U.S. PATENT DOCUMENTS

| | | | |
|---|---|---|---|
| 7,993,391 | B2 | 8/2011 | Stinson |
| 8,057,537 | B2 | 11/2011 | Zilla et al. |
| 8,715,340 | B2 | 5/2014 | Rudakov et al. |
| 9,132,003 | B2 | 9/2015 | Bar et al. |
| 9,237,945 | B2* | 1/2016 | El-Kurdl ............ A61L 27/3804 |
| 9,603,729 | B2* | 3/2017 | Soletti ............... A61B 17/11 |
| 10,076,427 | B2* | 9/2018 | Soletti ............... A61B 17/11 |
| 10,149,750 | B2* | 12/2018 | Wagner ............. A61L 27/047 |
| 10,335,519 | B2* | 7/2019 | Kaplan .............. A61B 5/6868 |
| 2004/0092976 | A1* | 5/2004 | Mowry ............... A61F 2/064 606/153 |
| 2006/0085063 | A1* | 4/2006 | Shastri .............. A61L 27/383 623/1.49 |
| 2009/0306770 | A1 | 12/2009 | Kassab |
| 2011/0124951 | A1 | 5/2011 | Walsh |
| 2011/0196475 | A1 | 8/2011 | Kitaoka et al. |
| 2013/0131780 | A1 | 5/2013 | Armstrong et al. |
| 2014/0284827 | A1 | 9/2014 | Pokorny et al. |
| 2015/0112419 | A1 | 4/2015 | Ahn et al. |
| 2015/0359619 | A1 | 12/2015 | Lelkes et al. |
| 2017/0216062 | A1 | 8/2017 | Armstrong et al. |
| 2017/0312102 | A1 | 11/2017 | Mangiardi |
| 2019/0365953 | A1* | 12/2019 | Turng ................ A61L 27/48 |
| 2020/0237494 | A1* | 7/2020 | El-Kurdi ............ A61F 2/06 |
| 2021/0236260 | A1* | 8/2021 | MacTaggart ........ A61F 2/07 |
| 2021/0338412 | A1* | 11/2021 | MacTaggart ....... B29C 53/56 |
| 2022/0047783 | A1* | 2/2022 | Hall .................. A61F 2/82 |
| 2023/0310002 | A1* | 10/2023 | Woods ............... A61L 31/16 606/152 |

FOREIGN PATENT DOCUMENTS

| | | |
|---|---|---|
| WO | WO 2014/143866 | 9/2014 |
| WO | WO 2015/126768 | 8/2015 |
| WO | WO 2018/200972 | 11/2018 |
| WO | WO 2019/213161 | 11/2019 |

OTHER PUBLICATIONS

Albertini et al., "Long-term results of arterial allograft below-knee bypass grafts for limb salvage: A retrospective multicenter study," J Vasc Surg., Mar. 2000, 31(3):426-435.

Andrews et al., "Placement of a flexible endovascular stent across the femoral joint: An in vivo study in the swine model," J Vasc Interv Radiol., Oct. 1999, 10(9):1219-1228.

Ansari et al., "Design considerations for studies of the biomechanical environment of the femoropopliteal arteries," J Vasc Surg., Sep. 2013, 58(3):804-813.

Bergmeister et al., "Biodegradable, thermoplastic polyurethane grafts for small diameter vascular replacements," Acta Biomater., Jan. 2015, 11:104-113.

Biemans et al., "Beware the kinking bypass—A hidden cause of graft reocclusion," EJVES Extra., May 2002, 3(5):88-90.

Bisdas et al., "Results of peripheral bypass surgery in patients with critical limb ischemia (CRITISCH registry)," Gefasschirurgie, 2016, 21(Suppl 2):S71-79.

Carter et al., "Morphologic characteristics of lesion formation and time course of smooth muscle cell proliferation in a porcine proliferative restenosis model," J Am Coll Cardiol., Nov. 1994, 24(5):1398-1405.

Chakfe et al., "The impact of knee joint flexion on infrainguinal vascular grafts: an angiographic study," Eur J Vasc Endovasc Surg., Jan. 1997, 13(1):23-30.

Charanpreet et al., "Medical Textiles as Vascular Implants and Their Success to Mimic Natural Arteries," Journal of Functional Biomaterials, Jun. 2015, 6:500-525.

Chatzizisis et al., "Role of endothelial shear stress in the natural history of coronary atherosclerosis and vascular remodeling: molecular, cellular, and vascular behavior," J Am Coll Cardiol., Jun. 2007, 49(25):2379-2393.

Chesnutt and Han, "Effect of Red Blood Cells on Platelet Activation and Thrombus Formation in Tortuous Arterioles," Front Bioeng Biotechnol., Dec. 2013, 1(18): 12 pages.

Chew et al., "Bypass in the absence of ipsilateral greater saphenous vein: Safety and superiority of the contralateral greater saphenous vein," J Vasc Surg., 2002, 35:1085-1091, 14 pages.

Conte et al., "Results of Prevent III: a multicenter, randomized trial of edifoligide for the prevention of vein graft failure in lower extremity bypass surgery," J Vasc Surg., Apr. 2006, 43(4):742-751.

Courtney et al., "Design and analysis of tissue engineering scaffolds that mimic soft tissue mechanical anisotropy," Biomaterials, Jul. 2006, 27(19):3631-3638.

Desyatova et al., "Constitutive modeling of human femoropopliteal artery biaxial stiffening due to aging and diabetes," Acta Biomater., Dec. 2017, 64:50-58, 9 pages.

Desyatova et al., "Effect of aging on mechanical stresses, deformations, and hemodynamics in human femoropopliteal artery due to limb flexion," Biomech Model Mechanobiol., 2017, 17(1):181-189, 9 pages.

Desyatova et al., "Limb flexion-induced twist and associated intramural stresses in the human femoropopliteal artery," J R Soc Interface., Mar. 2017, 14(128):20170025, 11 pages.

Desyatova et al., "The choice of a constitutive formulation for modeling limb flexion-induced deformations and stresses in the human femoropopliteal arteries of different ages," Biomech Model Mechanobiol., Jun. 2017, 16(3):775-785.

Desyatova, "Cross-sectional pinching in human femoropopliteal arteries due to limb flexion, and stent design optimization for maximum cross-sectional opening and minimum intramural stresses," J R Soc Interface., 2018, 15:20180475, 12 pages.

Edelman and Rogers, "Pathobiologic responses to stenting," Am J Cardiol., Apr. 1998, 81(7A):4E-6E.

EP Extended European Search Report in European Appln. No. 19796029.7, dated May 18, 2021, 7 pages.

EPO Communication Pursuant to Rule 114(2) EPC in European Appln. No. 19796029.7, dated Feb. 15, 2022, 4 pages.

Favreau et al., "Acute reductions in mechanical wall strain precede the formation of intimal hyperplasia in a murine model of arterial occlusive disease," J Vasc Surg., Nov. 2014, 60(5):1340-1347.

Feng et al., "Numerical Simulation of Thrombotic Occlusion in Tortuous Arterioles," J Cardiol Cardiovasc Med., Dec. 2017, 2(1):95-111.

Filipe et al., "Rapid Endothelialization of Off-the-Shelf Small Diameter Silk Vascular Grafts," JACC Basic Transl Sci., Feb. 2018, 3(1):38-53.

Fisher et al., "Below-knee PTFE bypass graft fatigue," Eur J Vasc Endovasc Surg., Sep. 1999, 18(3):266-267.

Guan et al., "Compliance Study of Endovascular Stent Grafts Incorporated with Polyester and Polyurethane Graft Materials in both Stented and Unstented Zones," Materials (Basel), Aug. 2016, 9(8):658, 15 pages.

Gupta et al., "Prospective, randomized comparison of ringed and nonringed polytetrafluoroethylene femoropopliteal bypass grafts: a preliminary report," J Vasc Surg., 1991, 13:163-72.

(56) References Cited

OTHER PUBLICATIONS

Hasan et al., "Electrospun Scaffolds for Tissue Engineering of Vascular Grafts—Review," Acta Biomater., Jan. 2014, 10(1)11-25.
Hollier et al., "Femoral anastomotic aneurysms," Ann Surg., Jun. 1980, 191(6):715-719.
Horný et al., "A comparison of age-related changes in axial prestretch in human carotid arteries and in human abdominal aorta," Biomech Model Mechanobiol., May 2016, 16(1):375-383, 9 pages.
Humphrey et al., "Fundamental role of axial stress in compensatory adaptations by arteries," J Biomech., Jan. 2009, 42:1-8.
International Preliminary Report on Patentability in International Appln. No. PCT/US2019/030041, dated Nov. 12, 2020, 7 pages.
International Preliminary Report on Patentability in International Appln. No. PCT/US2019/054401, dated Apr. 15, 2021, 8 pages.
International Search Report and Written Opinion in International Appln. No. PCT/US2019/030041, dated Jul. 2, 2019, 7 pages.
International Search Report and Written Opinion in International Appln. No. PCT/US2019/054401, dated Feb. 6, 2020, 11 pages.
Jackson et al., "Partial off-loading of longitudinal tension induces arterial tortuosity," Arterioscler Thromb Vasc Biol., 2005, 25:957-62.
Jackson et al., "Wall Tissue Remodeling Regulates Longitudinal Tension in Arteries," Circ Res., May 2002, 90(8):918-925, 9 pages.
Kamenskiy et al., "A mathematical evaluation of hemodynamic parameters after carotid eversion and conventional patch angioplasty," Am J Physiol Heart Circ Physiol., Sep. 2013, 305(5):H716-24.
Kamenskiy et al., "Age and disease-related geometric and structural remodeling of the carotid artery," J Vasc Surg., Dec. 2015, 62(6):1521-8.
Kamenskiy et al., "Comparative Analysis of the Biaxial Mechanical Behavior of Carotid Wall Tissue and Biological and Synthetic Materials Used for Carotid Patch Angioplasty," J Biomech Eng., Nov. 2011, 133(11):111008, 11 pages.
Kamenskiy et al., "Constitutive description of human femoropopliteal artery aging," Biomech Model Mechanobiol., 2017, 16(2):681-692.
Kamenskiy et al., "Effects of age on the physiological and mechanical characteristics of human femoropopliteal arteries," Acta Biomater., Nov. 2015:304-13.
Kamenskiy et al., "Hemodynamically Motivated Choice Of Patch Angioplasty For The Performance Of Carotid Endarterectomy," Ann Biomed Eng., Aug. 2012, 41(2):263-278, 16 pages.
Kamenskiy et al., "In situ longitudinal pre-stretch in the human femoropopliteal artery," Acta Biomater., Mar. 2016, 32:231-237.
Kamenskiy et al., "Passive biaxial mechanical properties and in vivo axial pre-stretch of the diseased human femoropopliteal and tibial arteries," Acta Biomater., Mar. 2014, 10(3):1301-1313.
Kamenskiy et al., "Patient demographics and cardiovascular risk factors differentially influence geometric remodeling of the aorta compared with the peripheral arteries," Surgery, 2015, 158(6):1617-1627, 11 pages.
Kamenskiy et al., "Prevalence of Calcification in Human Femoropopliteal Arteries and its Association with Demographics, Risk Factors, and Arterial Stiffness," Arterioscler Thromb Vasc Biol., Apr. 2018, 38(4):e48-e57, 9 pages.
Kapadia et al., "Modified prosthetic vascular conduits," Circulation, Apr. 2008, 117(14):1873-1882, 11 pages.
Kissin et al., "Vein interposition cuffs decrease the intimal hyperplastic response of polytetrafluoroethylene bypass grafts," J Vasc Surg., Jan. 2000, 31:69-83.
Lowe et al., "The Porcine Coronary Model of In-Stent Restenosis: Current Status in the Era of Drug-Eluting Stents," Catheter Cardiovasc Interv., Dec. 2003, 60(4):515-523.
Lundgren et al., "External support of a polytetrafluoroethylene graft improves patency for bypass to below-knee arteries," Ann Vasc Surg., Nov. 2013, 27(8):1124-1133.
MacTaggart et al., "Accepted Manuscript: Three-dimensional bending, torsion and axial compression of the femoropopliteal artery during limb flexion," J Biomech., Jul. 2014, 47(10):2249-2256, 27 pages.

MacTaggart et al., "Morphometric roadmaps to improve accurate device delivery for fluoroscopy-free resuscitative endovascular balloon occlusion of the aorta," J Trauma Acute Care Surg., Jun. 2016, 80(6):941-6.
MacTaggart et al., "Stent Design Affects Femoropopliteal Artery Deformation," Ann Surg., 2019, 270(1):180-187, 8 pages.
Mahoney et al., "One-year costs in patients with a history of or at risk for atherothrombosis in the United States," Circ Cardiovasc Qual Outcomes., Sep. 2008, 1(1):38-45, 10 pages.
Mahoney et al., "Vascular hospitalization rates and costs in patients with peripheral artery disease in the United States," Circ Cardiovasc Qual Outcomes., Nov. 2010, 3(6):642-51, 12 pages.
Maleckis et al., "Comparison of Femoropopliteal Artery Stents Under Axial and Radial Compression, Axial Tension, Bending, and Torsion Deformations," J Mech Behav Biomed Mater., Nov. 2017, 75:160-168.
Maleckis et al., "Nitinol Stents in the Femoropopliteal Artery: A Mechanical Perspective on Material, Design, and Performance," Ann Biomed Eng., May 2018, 46(5):684-704, 21 pages.
Maleckis, "Towards Precision Nanomanufacturing for Mechanical Design: From Individual Nanofibers to Mechanically Biomimetic Nanofibrillary Vascular Grafts," Thesis for the degree of Doctor of Philosophy, University of Nebraska-Lincoln, School of Biomedical Engineering, Feb. 2017, 1 page (Abstract Only).
Malek et al., "Hemodynamic Shear Stress and Its Role in Atherosclerosis," JAMA, Dec. 1999, 282(21):2035-2042.
Mellander et al., "Healing of PTFE grafts in a pig model recruit neointimal cells from different sources and do not endothelialize," Eur J Vasc Endovasc Surg., Jul. 2005, 30(1):63-70.
Mithieux and Weiss, "Elastin," Adv Protein Chem., 2005, 70:437-61.
Morishima et al., "Prolonged sitting-induced leg endothelial dysfunction is prevented by fidgeting," Am J Physiol—Hear Circ Physiol., Jul. 2016, 311(1):H177-H182.
Pennel et al., "Accepted Manuscript: Transmural capillary ingrowth is essential for confluent vascular graft healing," Acta Biomater., Jan. 2018, 65:237-247, 38 pages.
Poulson et al., "Limb flexion-induced axial compression and bending in human femoropopliteal artery segments," J Vasc Surg., Feb. 2018, 67(2):607-613, 7 pages.
Restaino et al., "Endothelial dysfunction following prolonged sitting is mediated by a reduction in shear stress," Am J Physiol Heart Circ Physiol., Mar. 2016, 310(5):H648-H653.
Schillinger et al., "Balloon angioplasty versus implantation of nitinol stents in the superficial femoral artery," N Engl J Med., May 2006, 354(18):1879-1888.
Schillinger et al., "Sustained benefit at 2 years of primary femoropopliteal stenting compared with balloon angioplasty with optional stenting," Circulation, May 2007, 115(21):2745-9.
Sheriff et al., "High-shear stress sensitizes platelets to subsequent low-shear conditions," Ann Biomed Eng., Apr. 2010, 38(4):1442-1450.
Singh et al., "Importance of stent-graft design for aortic arch aneurysm repair," Bioengineering, Feb. 2017, 4(1):133-150.
Singh et al., "Medical textiles as vascular implants and their success to mimic natural arteries," Biomaterials, Jun. 2015, 6(3):500-525.
Suwandi et al., "Inducing tissue specific tolerance in autoimmune disease with tolerogenic dendritic cells," Clin Exp Rheumatol., 2015, 33:S97-S103.
Taylor et al., "Acute disruption of polytetrafluoroethylene grafts adjacent to axillary anastomoses: a complication of axillofemoral grafting," J Vasc Surg., Oct. 1994, 20:520-528.
Taylor et al., "Autogenous reversed vein bypass for lower extremity ischemia in patients with absent or inadequate greater saphenous vein," Am J Surg., May 1987, 153(5):505-510.
Thosar et al., "Effect of prolonged sitting and breaks in sitting time on endothelial function," Med Sci Sports Exerc., Apr. 2015, 47(4):843-849.
Vasita and Katti, "Nanofibers and their applications in tissue engineering," Int J Nanomedicine, 2006, 1(1):15-30.

(56) References Cited

OTHER PUBLICATIONS

Vriens et al., "Superior two-year results of externally unsupported polyester compared to supported grafts in above-knee bypass grafting: A multicenter randomised trial," Eur J Vasc Endovasc Surg., 2013, 45(3):275-281.
Walsh et al., "Prolonged leg bending impairs endothelial function in the popliteal artery," Physiol Rep., Nov. 2017, 5(20):e13478, 8 pages.
Wang et al., "Biomimetic electrospun nanofibrous structures for tissue engineering," Mater Today, Jun. 2013, 16(6):229-241.
Watt, "Origin of femoro-popliteal occlusions," Br Med J., Dec. 1965, 2(5476):1455-1459.

\* cited by examiner

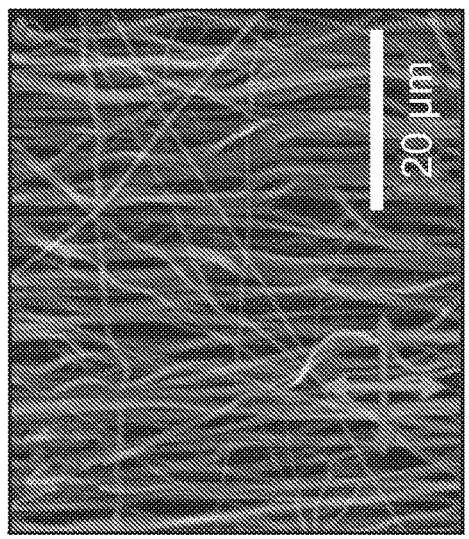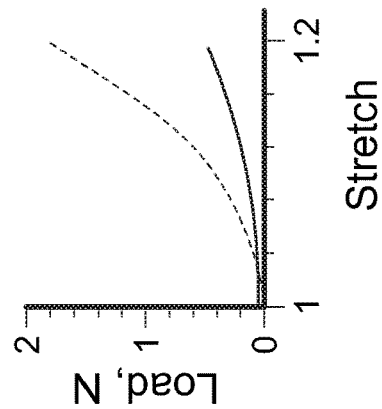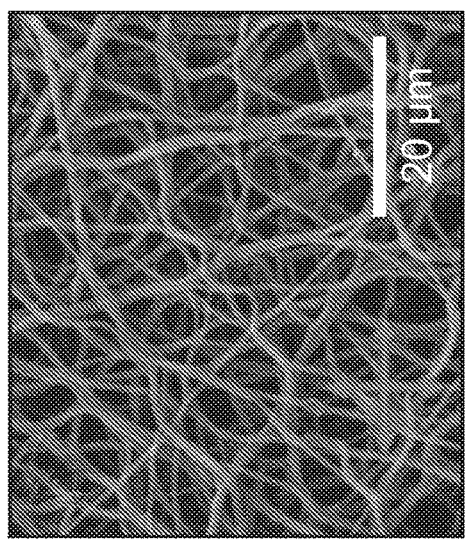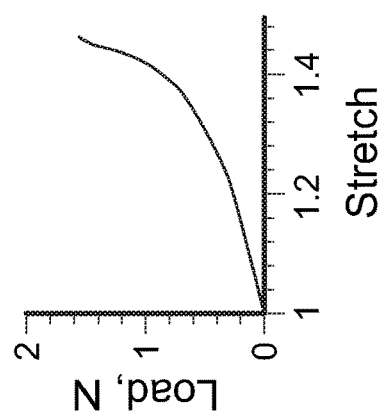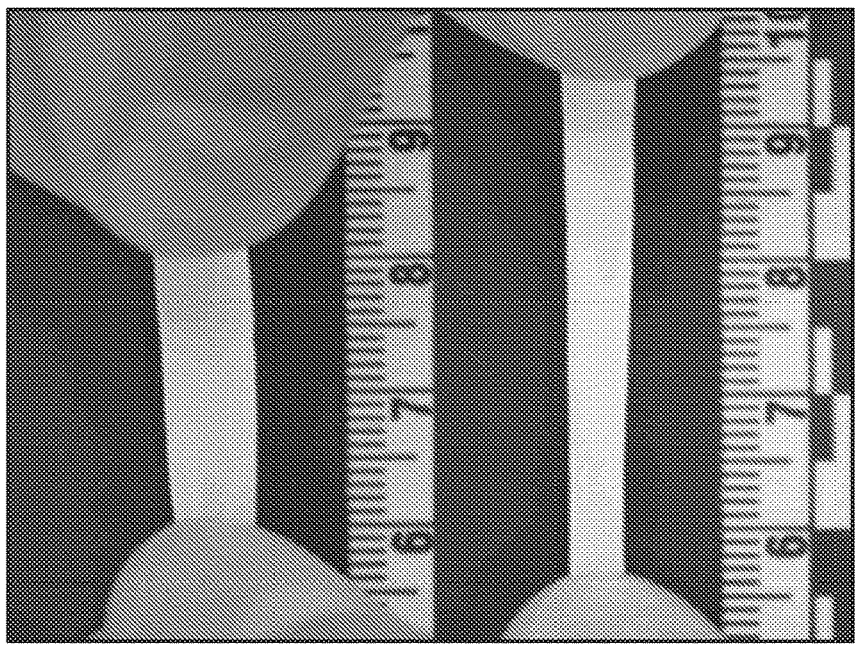
FIG. 6A  FIG. 6B  FIG. 6C

BYPASS GRAFT

CROSS-REFERENCE TO RELATED APPLICATIONS

This application is a National Stage Application under 35 U.S.C. § 371 and claims the benefit of International Application No. PCT/US2019/054401 filed Oct. 3, 2019, which claims priority under 35 U.S.C. § 119 to U.S. Provisional Application Ser. No. 62/741,828, filed on Oct. 5, 2018. The prior applications are hereby, which is incorporated by reference in its entirety-herein in their entireties.

TECHNICAL FIELD

This disclosure relates to apparatuses and methods for vascular bypass grafting.

BACKGROUND

Despite years of improvements and refinements in technologies and pharmacological adjuncts, failure rates remain high for lower extremity prosthetic grafts, particularly when the graft crosses the knee joint.

Young healthy arteries demonstrate specialized arrangement of the extracellular matrix components that creates axial tension also known as longitudinal pre-stretch (LPS). LPS appears to play a fundamental role in vascular mechanobiology. In young arteries, LPS may prevent arterial buckling during limb or end organ movement. In older arteries that have degraded and fragmented longitudinal elastin, LPS is significantly reduced. Diminished LPS does not allow the artery to optimally accommodate limb flexion-induced or organ-induced compression, which results in more severe bending, kinking, high intramural stresses, and disturbed flow; promoting deleterious cellular and biochemical responses that may culminate in both primary disease development and reconstruction failure.

SUMMARY

While LPS reduction in patients with arterial disease likely cannot be restored, this disclosure describes how LPS can be engineered into synthetic bypass grafts. In an example implementation, this disclosure describes an elastomeric bypass graft (EBG) (such as, but not limited to, a nanofibrillar elastomeric bypass) graft that can be pre-stretched, is able to accommodate limb flexion-induced or organ-induced deformations without kinking, and maintains anastomotic tension at or below the physiologic level.

Preliminary testing demonstrates significantly less tortuosity of EBGs used for lower extremity repair during limb flexion, improved flow patterns within these grafts compared to ePTFE grafts, and physiologic stress at the anastomosis. Therefore, longitudinally pre-stretched EBGs described herein are expected to demonstrate improved hemodynamics and produce better healing responses in the harsh biomechanical environment of the lower limbs, compared to conventional ePTFE grafts.

In one aspect, this disclosure is directed to a vascular bypass graft. The vascular bypass graft can include an elongate tubular graft made of an elastomeric material. The elastomeric material can comprise a network of nanofibers arranged to cause the tubular graft to exhibit non-linear elastic compliance in response to increasing longitudinal tensile loads.

Such a vascular bypass graft may optionally include one or more of the following features in any combination(s). The elastomeric material may comprise a nanofibrillar elastomeric material. In some embodiments, the network of nanofibers is arranged to cause the tubular graft to exhibit anisotropic properties. The anisotropic properties may include a greater longitudinal compliance than radial compliance. The vascular bypass graft may also include one or more reinforcing elements disposed between an inner layer of the elastomeric material and an outer layer of the elastomeric material, or on an outer surface of the outer layer of the elastomeric material. The one or more reinforcing elements may comprise an undulating wire spirally wrapped between the inner and outer layers of the elastomeric material. The one or more reinforcing elements may comprise an elongate element spirally wrapped between the inner and outer layers of the nanofibrillar elastomeric material. The one or more reinforcing elements may comprise an elongate polyethylene terephthalate element spirally wrapped between the inner and outer layers of the nanofibrillar elastomeric material. The vascular bypass graft may also include a first pre-stretch regulator coupled to a first end portion of the tubular graft and a second pre-stretch regulator coupled to a second end portion of the tubular graft. In some embodiments, the first and second pre-stretch regulators comprise tethers. The vascular bypass graft may also include one or more wings extending laterally from the tubular graft.

In another aspect, this disclosure is directed to a method of implanting a blood vessel bypass graft. The method of implanting the blood vessel bypass graft may include creating a first anastomosis between a vascular bypass graft and a native blood vessel; and creating a second anastomosis between the vascular bypass graft and the native blood vessel. The vascular bypass graft may comprise an elastomeric material made of a network of nanofibers arranged to cause the vascular bypass graft to exhibit non-linear elastic compliance in response to increasing longitudinal tensile loads.

Such a method of implanting a blood vessel bypass graft may optionally include one or more of the following features in any combination(s). The method may also include longitudinally pre-stretching the vascular bypass graft so that the vascular bypass graft is in tension between the first and second anastomoses. The method may also include attaching to the native blood vessel a first pre-stretch regulator that is coupled to a first end portion of the vascular bypass graft. The method may also include attaching to the native blood vessel a second pre-stretch regulator that is coupled to a second end portion of the vascular bypass graft. The method may also include attaching to the native blood vessel one or more wings that extend laterally from the vascular bypass graft. In some cases, the native blood vessel is a femoropopliteal artery.

In another aspect, this disclosure is directed to a method of making a prosthetic blood vessel bypass graft. The method of making the prosthetic blood vessel bypass graft includes: (i) depositing a first layer of elastomeric material onto a rotating mandrel, wherein the elastomeric material comprises polyether-based urethane; (ii) positioning one or more reinforcing framework members on the first layer; and (iii) depositing a second layer of the elastomeric material onto the first layer and the one or more reinforcing framework members while the mandrel is rotating.

Such a method of making a prosthetic blood vessel bypass graft may optionally include one or more of the following features in any combination(s). The method may result in the prosthetic blood vessel bypass graft exhibiting non-linear elastic compliance in response to increasing longitudinal tensile loads. At least one of the depositing the first layer of the elastomeric material or the depositing the second layer of the elastomeric material may comprise electrospinning. The method may also include controlling fiber undulation of the nanofibrillar elastomeric material to attain a desired level of the non-linear elastic compliance. The method may result in the prosthetic blood vessel bypass graft exhibiting anisotropic properties comprising a greater longitudinal compliance than radial compliance.

Potential advantageous benefits of one or more of the implementations described in the present specification may include improved patient outcomes following vessel bypass graft implantation. The one or more implementations may provide improved blood flow following graft implantation. The EBGs described herein can be pre-stretched and are able to accommodate limb flexion-induced or organ-induced deformations without excessive tortuosity or kinking. This novel mechanical adjustment to synthetic bypass grafts is expected to lead to more durable reconstructions for patients with claudication and critical limb ischemia, improving limb function and reducing reinterventions.

It is appreciated that methods in accordance with the present disclosure may include any combination of the aspects and features described herein. That is, methods in accordance with the present disclosure are not limited to the combinations of aspects and features specifically described herein, but also include any combination of the aspects and features provided.

The details of one or more implementations of the subject matter of this disclosure are set forth in the accompanying drawings and the description below. Other features, objects, and advantages of the subject matter will be apparent from the description and drawings, and from the claims.

DESCRIPTION OF DRAWINGS

FIG. 6 shows images and graphs illustrating that by using blends of biocompatible and hydrolysis-resistant polyurethanes with different residual deformations, undulations in nanofibers are induced and controlled, producing a elastically compliant graft fabric with a non-linear stiffening response under increasing tensile loads.

DETAILED DESCRIPTION

This disclosure describes new prosthetic bypass grafts and methods for treating conditions such as, but not limited to, PAD. Bypass grafts described herein which can simulate LPS can be used in all arterial beds that require bypass grafting, including (but are not limited to) lower and upper extremity, iliac, renal, coronary, carotid, subclavian artery, or aortic beds; however lower extremity applications are a particularly advantageous usage.

Figures 1A, 1B:
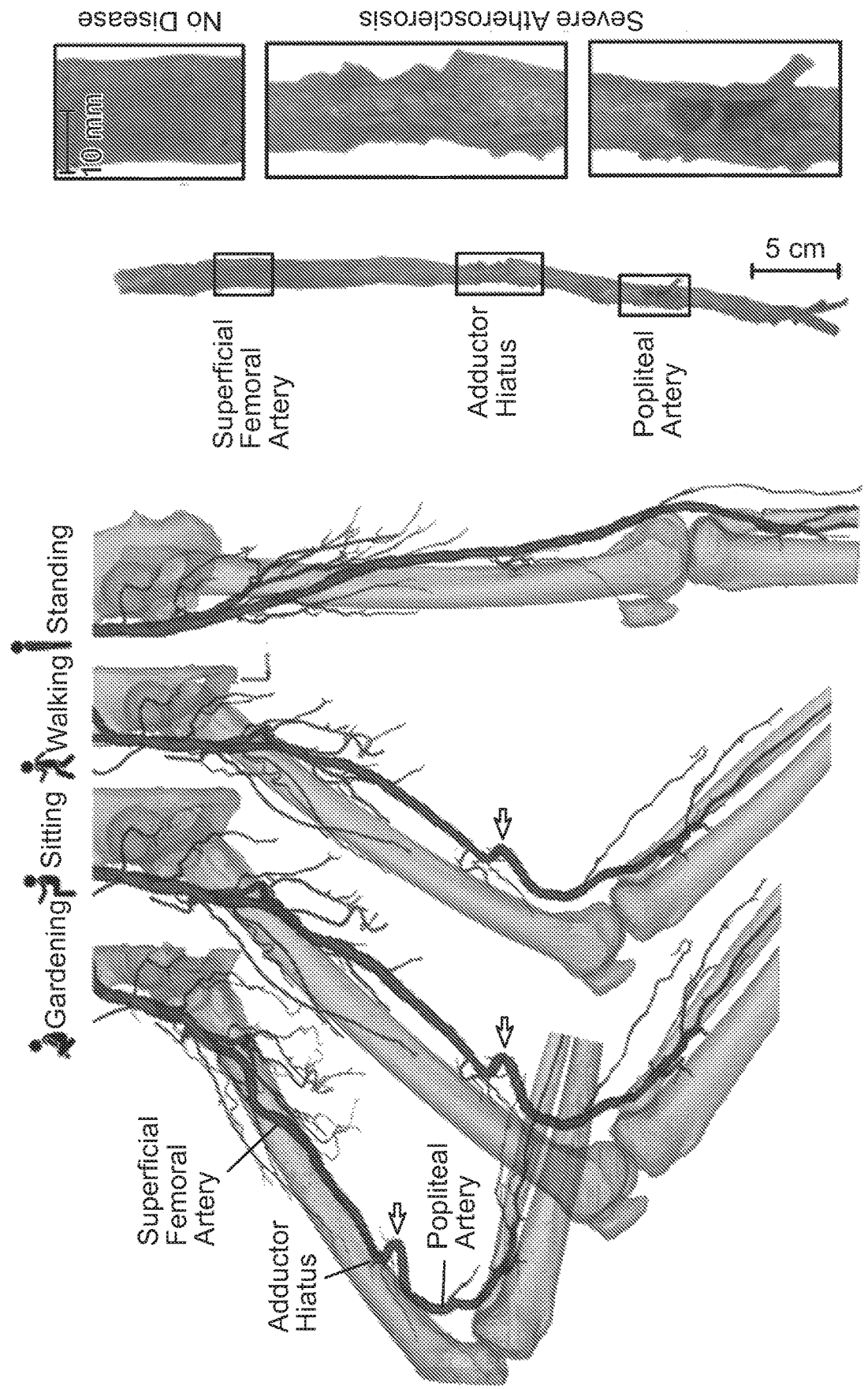
FIG. 1A illustrates four different postures of a leg and shows how bending of the lower limb can cause the artery to kink at the adductor hiatus location.
FIG. 1B shows an artery that includes a superficial femoral artery, a segment of the distal superficial femoral/proximal popliteal artery at the adductor hiatus, and the popliteal artery, and that exhibits atherosclerosis in a portion of the popliteal artery.

Referring to FIGS. 1A and 1B, the FPA begins as the common femoral artery (not shown) and continues as the superficial femoral artery (SFA) into the upper thigh. It becomes the popliteal artery (PA) as it traverses the adductor hiatus (AH), a gap between the adductor magnus muscle and the femur, passing from the anterior thigh posteriorly into the popliteal fossa behind the knee. Two possible sites of pre-stretched graft bypass applications can be the distal SFA at the AH and the PA below the knee.

Major differences between the FPA and other arterial segments are slower flow rates and more severe deformations experienced by the FPA during flexion of the limbs, as illustrated in FIG. 1A. The inventors claim that use of the pre-stretched bypass graft in these locations can improve flow characteristics and patency compared to conventional FPA bypass grafts.

Figures 2A, 2B:
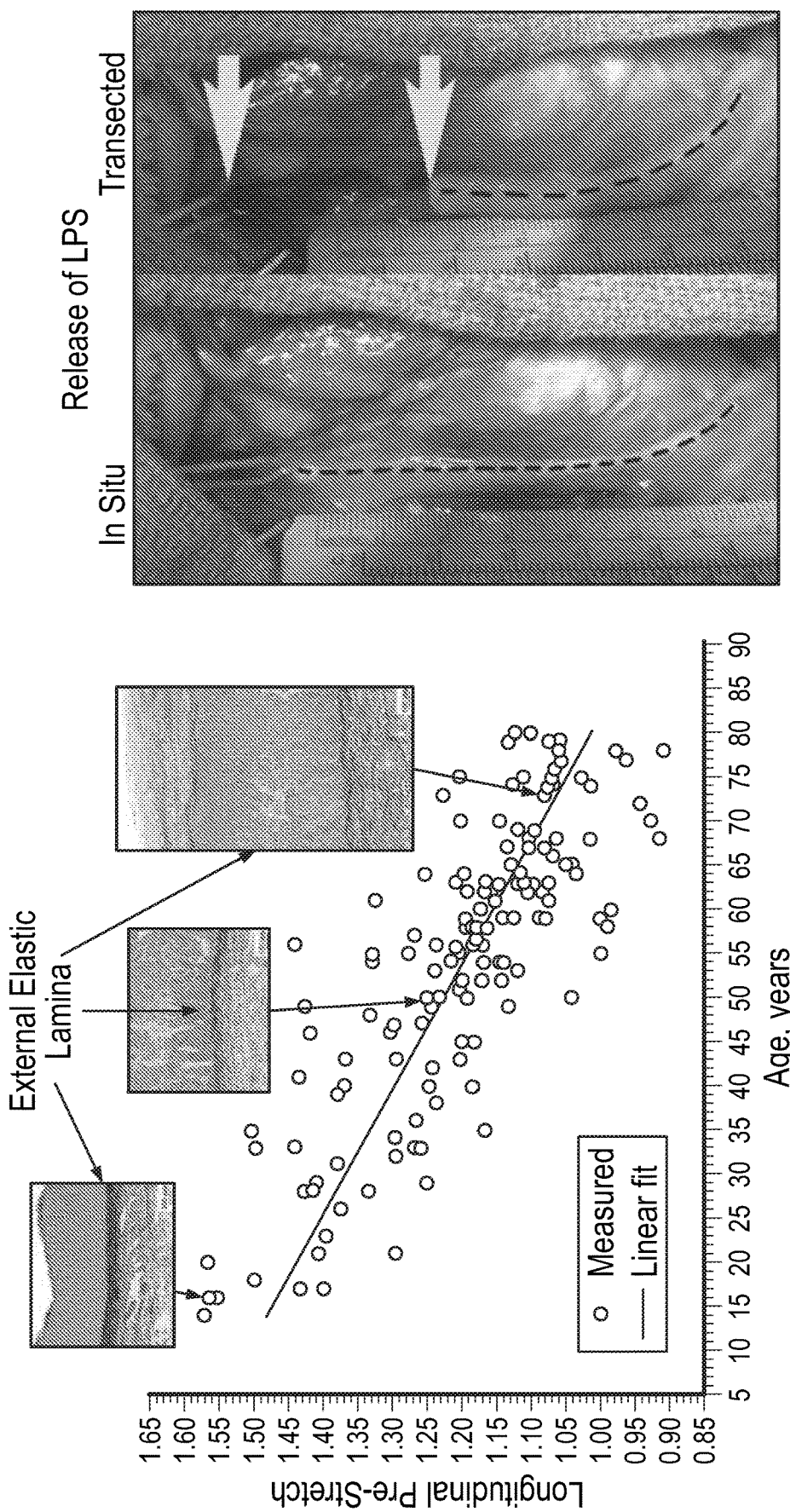
FIG. 2A is a graph showing longitudinal pre-stretch of an artery in relation to patient age.
FIG. 2B shows how longitudinal pre-stretch releases when an artery is transected.

Referring to FIGS. 2A and 2B, longitudinal pre-stretch (LPS) is an important physiological characteristic of healthy arteries. The magnitude of the LPS is known to decrease with age and is associated with changes in the microstructure (FIG. 2A). LPS can be assessed by measuring foreshortening of the artery after transection which releases pre-stretch (FIG. 2B). For example, an in situ vessel length measuring 15 cm that foreshortens to an excised length of 10 cm has LPS of 1.5.

LPS plays a fundamental role in arterial mechanics. The FPA demonstrates significantly different structural features and mechanical properties compared to other arteries. The specialized arrangement of the extracellular matrix components creates longitudinal tension within the healthy FPA in magnitudes that have not been demonstrated in other arteries. In the inventor's experiments described below, LPS was found to facilitate energy efficient arterial function by decoupling internal pressure and axial force, providing important mechanical cues, and acting as an energy reserve for adaptive remodeling.

Figure 3:
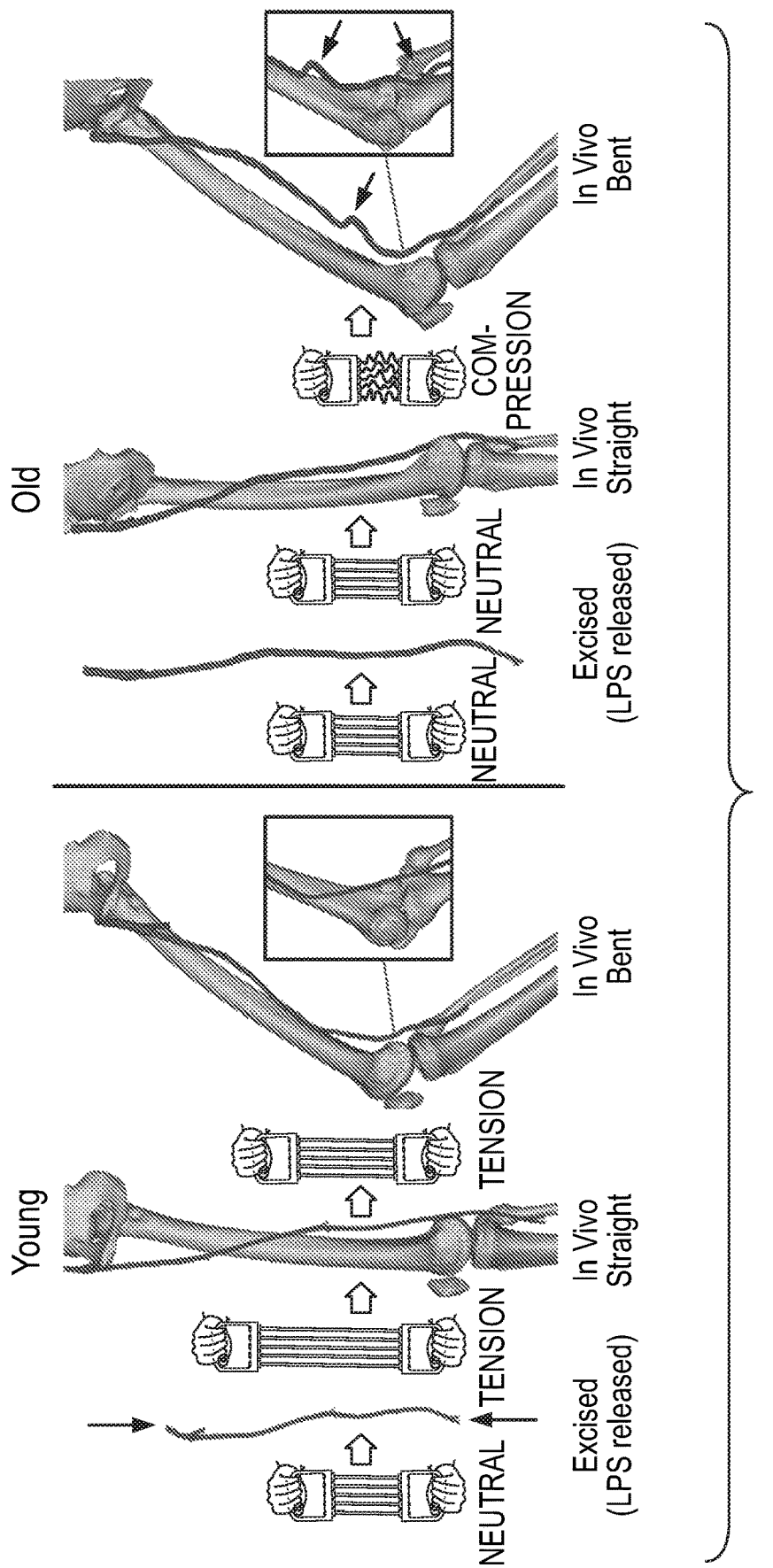
FIG. 3 shows images that illustrate how reductions of longitudinal pre-stretch with age have significant effects on the shape of arteries in the flexed limb posture.

Also referring to FIG. 3, reductions of LPS with age have significant effects on the shape of the artery in the flexed limb posture. Said another way, LPS reduces limb flexion-induced bending and kinking of the FPA, promotes better hemodynamics, and lower intramural stresses. FIG. 3 illustrates deformations of the FPA with limb flexion in representative young and old subjects. Note FPA kinking at the adductor hiatus and in the popliteal artery in the old subject, likely due to loss of LPS.

In the straight limb posture the young in vivo FPA is under tension, i.e. has LPS, while old FPA is not (it is neutral). Limb flexion partially offloads the young artery longitudinally, but some tension remains thereby preventing kinking. Since LPS is almost completely absent in the old FPA (i.e., the artery would not foreshorten upon excision), there is no tension left in the artery to prevent kinking in the flexed limb.

One of the roles of LPS in the lower limb arteries is prevention of arterial tortuosity and kinking during limb flexion. In young healthy arteries (FIG. 3, left portion), the LPS is large, which likely helps keep the artery in tension even in the flexed limb, thereby reducing kinks and tortuosity, and facilitating better hemodynamics and lower intramural stresses.

Still referring to FIG. 3, FPA kinking at the AH and in the PA is evident in the old subject (right portion of FIG. 3), due to loss of LPS. The illustrated chest expander analogy (i.e., labeled "neutral," "tension," or "compression") illustrates LPS in excised and in vivo states. In the straight limb posture the young in vivo FPA is under tension, i.e., has LPS, while old FPA is not (it is neutral). Limb flexion ("bent") partially offloads the young artery longitudinally, but some tension remains thereby preventing kinking. Since LPS is almost completely absent in the old FPA (i.e., the artery would not foreshorten upon excision), when bent, there is no tension left in the artery to prevent kinking in the flexed limb.

Embodiments of the elastomeric bypass grafts described herein have the capability of producing tunable amounts of stretch and tension at different segments of the graft. LPS potentially facilitates energy efficient arterial function by decoupling internal pressure and axial force, provides important mechanical cues for arterial healing, potentially acts as an energy reserve for adaptive remodeling, and prevents development of tortuosity and aberrant matrix metalloproteinase activity. Incorporating LPS into bypass grafts to reduce bending and tortuosity of the graft during limb flexion or organ movement can improve hemodynamics, healing, and patency. This novel mechanical adjustment to synthetic bypass grafts could lead to more durable reconstructions for patients requiring bypass grafts.

The inventors have developed novel elastomeric bypass grafts (EBGs) (such as, but not limited to, nanofibrillar elastomeric bypass (NEB) grafts) that can be longitudinally stretched while maintaining physiologic longitudinal tension. Herein, the bypass grafts may be referred to as EBG/NEB grafts. It should be understood that the NEB grafts are one non-limiting example type of the EBGs described herein. Other types of EBGs are also included in the scope of this disclosure.

EBG/NEB grafts resist kinking and can be longitudinally stretched to physiologic (LPS). In one example, electrospinning can be used to produce these EBGs. However, other manufacturing methods (e.g., weaving, 3D printing, casting, etc.) can also be used as long as the graft can reproduce physiologic pre-stretch while maintaining physiologic stresses. Various materials including synthetic and/or biological materials, and reinforcement element patterns can also be employed for making the EBGs.

New bypass grafts as disclosed herein having LPS capability will likely tend to promote better revascularization results. While conventional ePTFE bypass grafts are incapable of LPS, modern manufacturing techniques as described herein can be used to make materials with precisely tunable mechanical properties. Such materials can be made more compliant longitudinally to induce LPS without excessive anastomotic stresses, while also ensuring physiologic circumferential performance.

Over the past several years, the inventors have analyzed over 500 human FPAs 13-82 years old, permitting quantification of physiologic levels of LPS, axial force, and longitudinal and circumferential stresses and strains experienced by FPAs of different ages. The inventors have also characterized the deformations experienced by human FPAs during limb flexion, and have mapped out areas where these arteries experience the most severe bending and kinking. These data were used to invent a new-generation LPS-capable bypass graft that will reduce tortuosity and kinking during limb flexion, and promote better hemodynamics and improved healing responses compared with conventional ePTFE grafts.

Figure 4B:
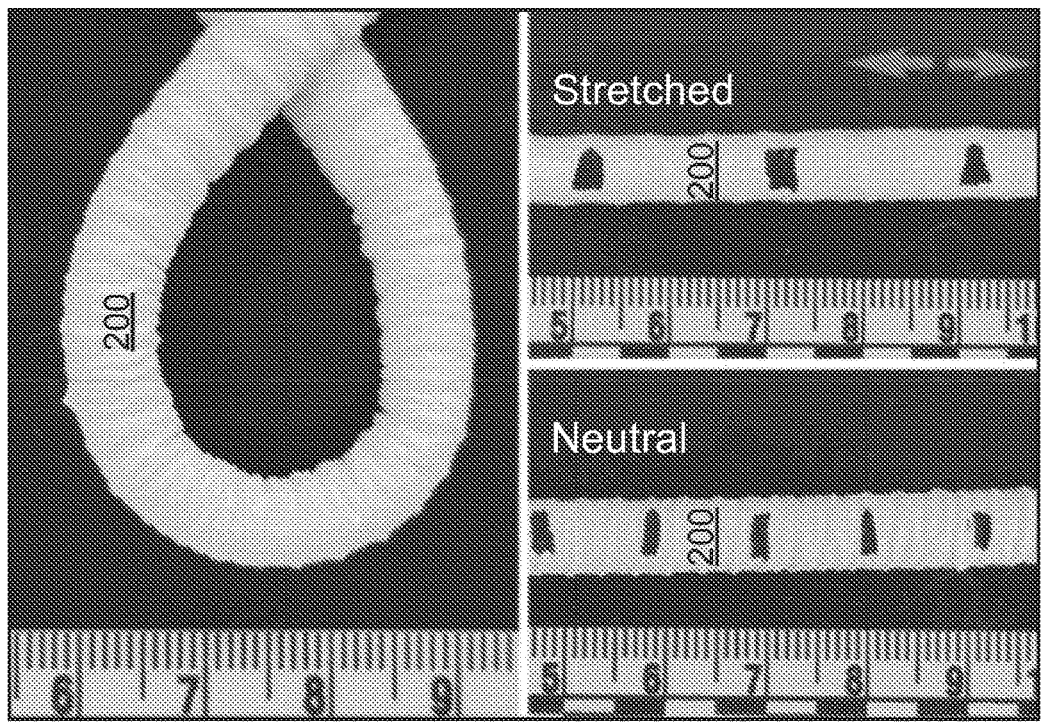
FIG. 4 depicts two example bypass grafts, in accordance with some embodiments.
Figure 4A:
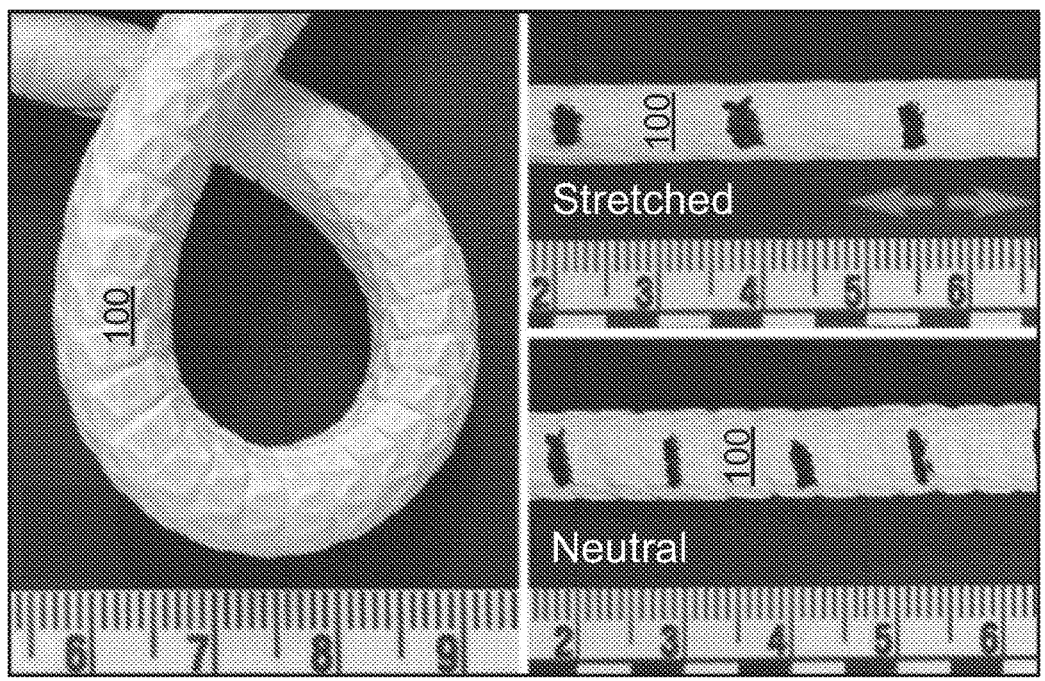

Referring to FIG. 4, the inventors have developed and produced new-generation biocompatible polyurethane-based EBGs. For example, EBG grafts 100 and 200 are shown. EBG graft 100 is reinforced with a winding of undulating nitinol element(s). EBG graft 200 is reinforced with a winding of linear polyethylene terephthalate (PET) element(s). The reinforcing elements help the grafts 100 and 200 to resist kinking and pinching (as illustrated in the upper panels of FIG. 4) while allowing the grafts 100 and 200 to be longitudinally stretched to emulate physiologic LPS (as illustrated in the lower panels of FIG. 4). The properties of the elastomeric material used for the grafts can be tuned to target specific levels of non-linear circumferential and longitudinal compliance, and anisotropy.

One unique aspect of the EBGs described herein (such as EBG grafts 100 and 200) pertains to the strategic controlling of the mechanical properties of the grafts. For example, mechanical properties of the grafts can be tuned by changing the undulation and orientation of the nanofibers in the network of the nanofibrillar elastomeric material of NEB grafts. This allows simultaneous control of the overall compliance and non-linear stiffening of the material under increasing loads. Simply making the material compliant results in its uncontrolled expansion under pressure, while non-linear stiffening replicates artery-like behavior and prevents overstretch. However, by controlling polymer ratios, nanofiber undulation, and wall thickness the inventors are able to vary the degree of non-linear compliance. Further, by controlling mandrel rotation speed the inventors can vary fiber alignment and the degree of anisotropy to fine-tune the mechanical properties. The degree of anisotropy is particularly important for reproducing LPS as human FPAs are anisotropic and are significantly more compliant longitudinally to accommodate LPS. As demonstrated below in the experimental summary, in addition to mimicking mechanical characteristics of the FPA, our elastomeric nanofibrillar material also becomes endothelialized and infiltrated with smooth muscle cells within two weeks of implantation in swine.

The EBG/NEB grafts described herein can be pre-stretched and are able to accommodate limb flexion-induced or organ-induced deformations without kinking. Preliminary testing has demonstrated significantly less tortuosity of EBG/NEB grafts used for lower extremity repair during limb flexion and improved flow patterns within these grafts compared to ePTFE grafts.

The EBG/NEB grafts described herein may be made from one or more polymers including, but not limited to, polymethacrylate, poly vinyl phenol, polyvinylchloride, cellulose, polyvinyl alcohol, polyacrylamide, poly(lactic-co-glycolic) acid (PLGA), collagen, polycaprolactone (PCL), polyurethanes (e.g. Pellethane® thermoplastic polyurethanes including but not limited to 2363-55DE, 2363-55D, and 5863-82A), polyvinyl fluoride, polyamide, silk, nylon, polybennzimidazole, polycarbonate, polyacrylonitrile, polyvinyl alcohol, polylactic acid, polyethylene-co-vinyl acetate, polyethylene oxide, polyaniline, polystyrene, polyvinylcarbazole, polyethylene terephthalate, polyacrylic acid-polypyrene methanol, poly(2-hydroxyethyl methacrylate), polyether imide, polyethylene gricol, polyethylene glycol, poly(ethylene-co-vinyl alcohol), polyacrylnitrile, polyvinyl pyrrolidone, polymetha-phenylene isophthalamide, gelatin, alginate, chitosan, starch, pectin, cellulose, methylcellulose, sodium polyacrylate, and starch-acrylonitrile co-polymers. In one embodiment the polymer is a polyurethane based polymer. In one embodiment the polymer is an elastomeric polymer.

The EBG/NEB grafts described herein may also contain an embedded or surrounding scaffold of one or more reinforcing elements. Such a scaffold may be made out of a variety of materials including but not limited to Nitinol, magnesium and magnesium alloys/mixtures (including biodegradable forms of magnesium), plastics (biodegradable and non-biodegradable), metals and various metal alloys, and other polymers (such as Polyethylene Terephthalate), or combinations of various polymers. The scaffold may be made in a variety of patterns including but not limited to the patterns shown in the right panels of FIG. 10. For example, in some example embodiments the scaffold of reinforcing elements may comprise multiple rings made of elongate elements (e.g., wires) that are positioned adjacent to each other while being distinct from each other. In other examples, the scaffold of reinforcing elements may be spirally wound around/along the graft.

Figure 11:
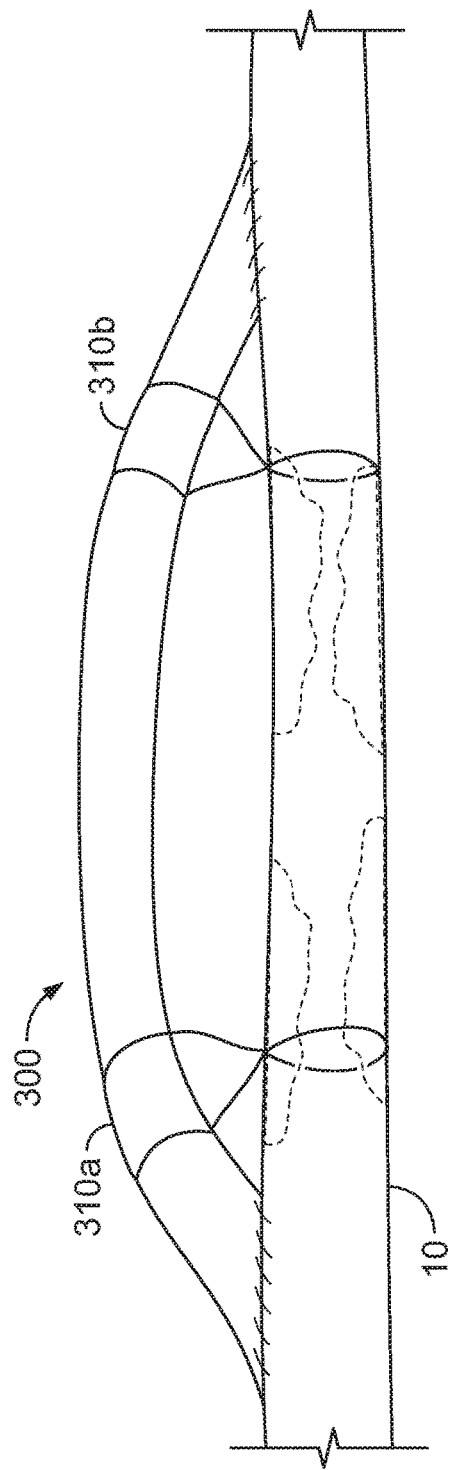
FIG. 11 illustrates an example bypass graft in accordance with some embodiments.
Figure 12:
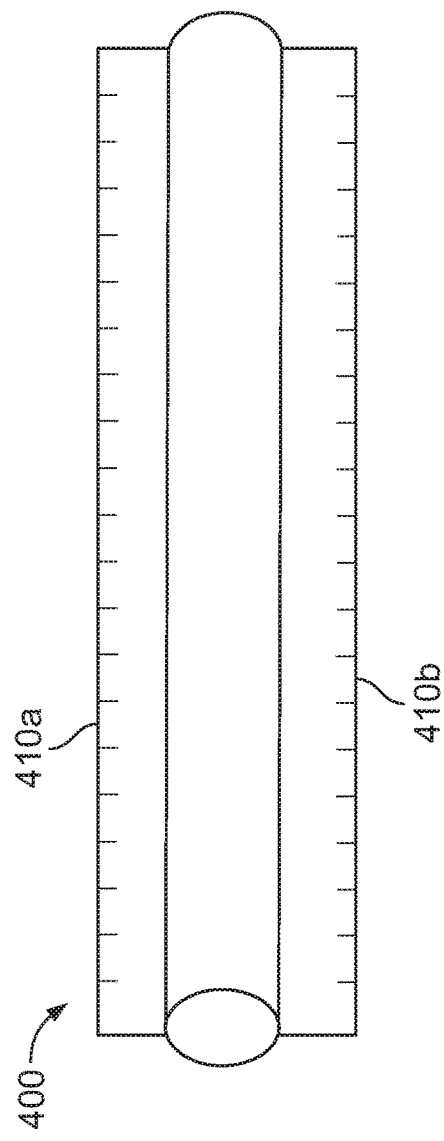
FIG. 12 illustrates another example bypass graft in accordance with some embodiments.

Referring to FIGS. 11 and 12, in some embodiments the EBG/NEB grafts described herein may also contain one or more pre-stretch regulators and/or one or more petals/wings. For example, the EBG/NEB graft 300 includes a first pre-stretch regulator 310a and a second pre-stretch regulator 310b. The pre-stretch regulators 310a-b can be used to tether end portions of the graft 300, near the anastomoses, to the native vessel 10. In another example, the EBG/NEB graft 400 includes a first wing 410a and a second wing 410b. The wings 410a-b can be used to attach end portions of the graft 400 to a native vessel (in addition to the anastomoses).

While in the depicted example includes two wings 410a-b that are rectangular in shape, in some embodiments the wings 410a and/or 410b can have different shapes, sizes, or numbers. For example, in some embodiments either or both of the wings 410a-b can vary in width along the length of the wings 410a-b. The sizes of the wings 410a-b and the number of wings can also be varied.

The pre-stretch regulators 310a-b and/or wings 410a-b can also be used to allow precise and differential tuning of tension and/or compliance at each anastomosis and along the middle body of the EBG/NEB grafts. The pre-stretch regulators 310a-b and wings 410a-b help reduce the stretch-induced force on the anastomosis, while keeping the EBG/NEB grafts pre-stretched to the desired level. Pre-stretch regulators 310a-b or wings 410a-b can be attached to a diseased part of the bypassed artery 10 or to the surrounding tissues. The pre-stretch regulators 310a-b and wings 410a-b can be made from a variety of materials including but not limited to polymers (such as non-elastomeric polymers), plastics, and metal alloys.

Some embodiments of the bypass grafts with tunable LPS as described herein include: i) a compliant graft with mechanical properties that can be tuned to mimic mechanical properties of vascular tissues, ii) an embedded scaffold used to reinforce the graft and avoid excessive tortuosity and kinking in dynamic environments, such as that of the lower extremity, and, optionally, iii) means of graft attachment that allow tunable amounts within different segments of the graft (e.g., pre-stretch regulators 310a-b and/or wings 410a-b that facilitate different tensions at the anastomoses versus within the middle portion of the graft).

Applications for the EBG/NEB bypass grafts described herein include (but are not limited to) lower and upper extremity, iliac, renal, coronary, carotid, subclavian artery, or aortic beds. Detailed descriptions of example bypass grafts are provided herein in the context of treating vessels in lower extremity applications (i.e., the femoropopliteal artery, FPA), but the same concepts can be used in other arterial beds, as well as for other uses, and/or using substitute or additional materials.

SUMMARY OF DESIGN AND DEVELOPMENT EXPERIMENTATION

The inventors have performed experimental studies to validate the inventive bypass graft designs and method of treatment concepts disclosed herein.

INTRODUCTION: LPS plays a paramount role in normal arterial physiology and provides mechanical cues that can drive arterial remodeling. For example, LPS is useful for preventing the development of tortuosity and aberrant matrix metalloproteinase activity, and in the lower limbs LPS facilitates normal hemodynamics and intramural stresses. In these experimental studies, the inventor's elastomeric grafts were used to test the hypothesis that incorporating LPS into lower extremity bypass grafts to reduce bending and tortuosity of the graft during limb flexion which can potentially also lead to improved hemodynamics, healing, and patency. It was postulated that this novel mechanical adjustment to synthetic bypass grafts may lead to more durable reconstructions for PAD patients with claudication and critical limb ischemia, improving limb function and reducing re-interventions.

EXPERIMENTAL RESOURCES: The inventors have collected a database of FPA mechanical properties and LPS from over 500 human subjects 13-82 years old. This allowed the inventors to perform detailed bench-top and computational studies of physiologic stresses, strains, LPS, and longitudinal tethering forces specific to FPAs in different age groups with different risk factors. These data serve as a unique resource for fine-tuning the mechanical properties and LPS of synthetic NEBs that were developed and used in the study.

Mechanical stresses have paramount effects on arterial physiology, but they cannot be directly measured and require calculation using engineering techniques. Accordingly, the inventors developed a set of computational models that simulates limb flexion-induced arterial deformations that allow studies of intramural stresses, strains, and hemodynamics. These models proved instrumental in optimizing the mechanical characteristics of the NEBs to reduce tortuosity and kinking during limb flexion while ensuring physiologic stresses, strains, and optimal hemodynamics within the vessels.

Moreover, the inventors developed an advanced material capable of LPS that performs well in vivo. Additionally, the inventors developed a new manufacturing method to produce an artery-mimicking material that can accommodate LPS while maintaining physiologic stresses. The novelty of this approach is in utilizing blends of biocompatible polyurethanes that produce nanofiber undulation when combined in the nanofibrillar networks. When electro-spinning is used to manufacture the EBG grafts, control over polymer ratios, solution feed volumes, and rotation speed of the cylindrical collector allows for the manufacture of grafts with collagen-like fiber undulations similar to arterial tissue that produce a compliant fabric with a non-linear stiffening response under increasing loads that can be tuned separately for the longitudinal and circumferential directions. The inventors also established a new approach of manufacturing long EBG/NEB grafts with techniques for kink-resistant graft reinforcements, and methods for surgical implantation to reduce anastomotic tension.

Figure 5:
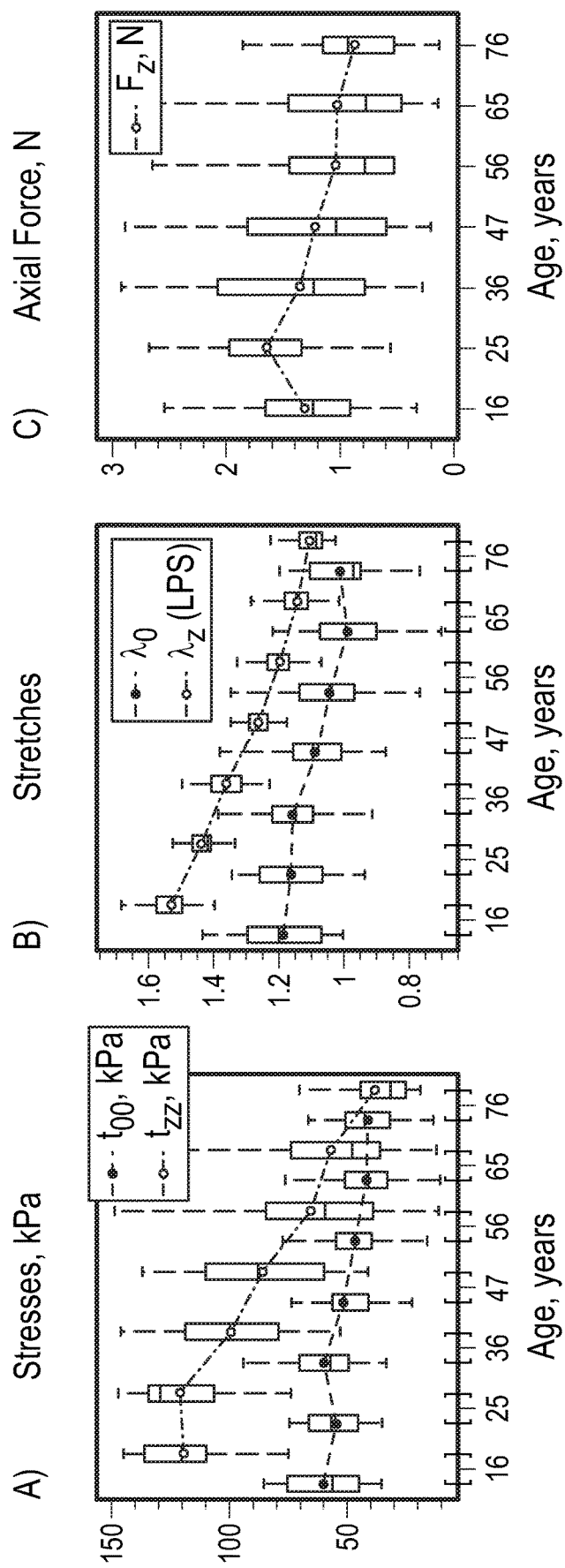
FIG. 5 shows three graphs that demonstrate how physiologic circumferential and longitudinal stresses (left graph), stretches including LPS (middle graph), and axial force associated with LPS (right graph) change with age. These graphs can be used to supply target values for stresses and stretches in the bypass grafts.

FIG. 5 demonstrates how physiologic circumferential and longitudinal stresses (left graph), stretches including LPS (middle graph), and axial force associated with LPS (right graph) change with age. In part, due to the presence of residual stresses/strains, most of these data cannot be directly measured in vivo, but they can be assessed using in situ/excised arterial length measurements, biaxially-determined mechanical properties, and constitutive modeling. These data inform the range of physiologic mechanical characteristics for young healthy FPAs that will guide the development of EBG/NEB grafts.

While other research teams may be working on nanofibrillar vascular graft materials, most use polymers such as Polyethylene Terephthalate (PET) that are unable to accommodate physiological stretches when subjected to physiological forces. The distinct feature of the inventor's manufacturing process of nanofibrillar elastomeric material is the precise control of force-stretch behavior of the material through manipulation of its microstructure.

As illustrated in FIG. 6, by using blends of biocompatible and hydrolysis-resistant polyurethanes with different residual deformations, the inventors are able to induce and control undulations in nanofibers, producing a compliant graft fabric with a non-linear stiffening response under increasing loads (see middle panel of FIG. 6), which is similar to the arterial non-linearity due to undulated collagen and elastic fibers. This important characteristic of arteries provides high deformability at low pressure, while preventing aneurysmal expansion under high pressure. Biaxial mechanical testing confirms that the fibrous structure resembling undulated intramural arterial collagen stiffened non-linearly, like an artery. Furthermore, mechanical anisotropy can be controlled by inducing nanofiber alignment circumferentially (see right panel of FIG. 6), which results in higher longitudinal compliance typical for FPAs while ensuring low axial force under large LPS.

Figure 7B:
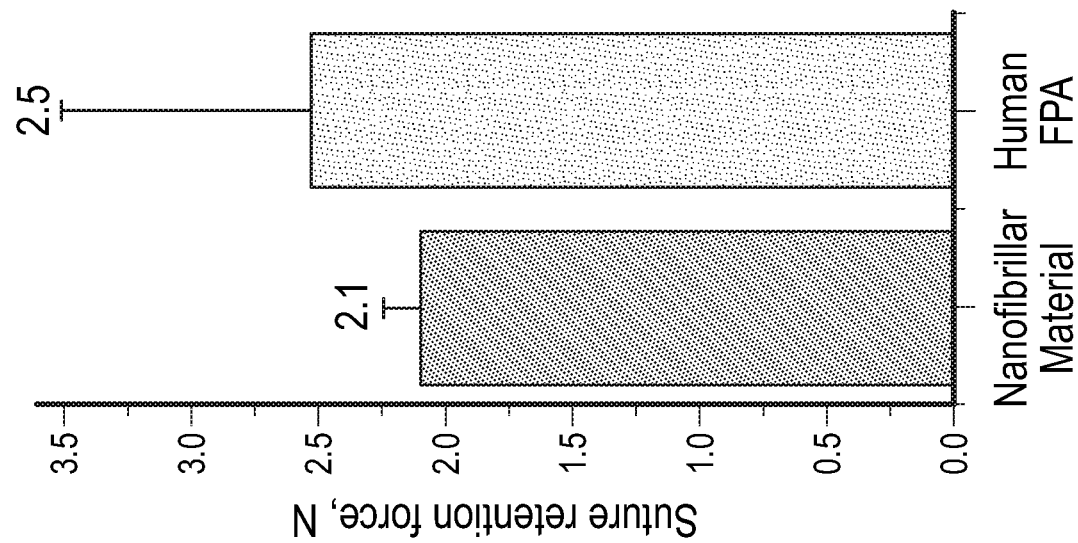
FIGS. 7A-D are graphs that illustrate that nanofibrillar elastomeric material does not require pre-clotting (FIG. 7A), exhibits high suture retention properties (FIG. 7B), is significantly stronger and tougher than human FPA in both circumferential and longitudinal directions FIG. 7C), and demonstrates excellent cell coverage and viability compared with conventional ePTFE when seeded with primary porcine smooth muscle cells at 7 days in culture (FIG. 7D).
Figure 7A:
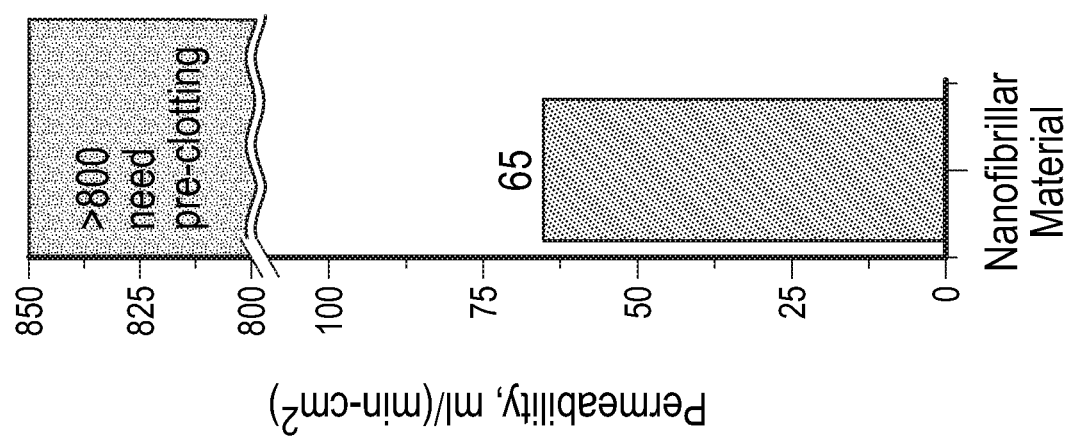
Figures 7C, 7D:
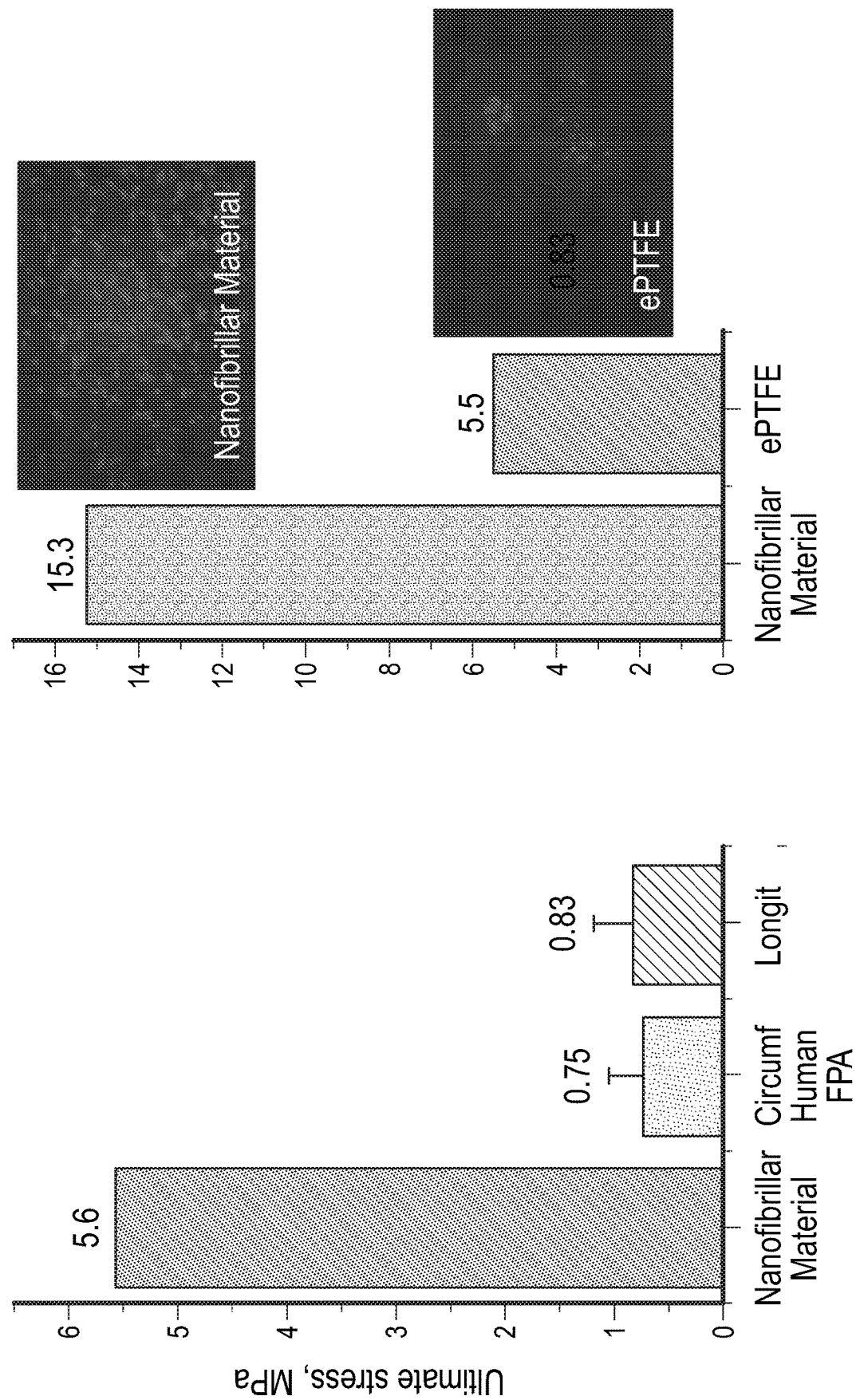

Referring to FIGS. 7A-7D, nanofibrillar elastomeric material does not require pre-clotting (FIG. 7A), exhibits high suture retention properties (FIG. 7B), is significantly stronger and tougher than human FPA in both circumferential and longitudinal directions FIG. 7C), and demonstrates excellent cell coverage and viability compared with conventional ePTFE when seeded with primary porcine smooth muscle cells at 7 days in culture (FIG. 7D). The inserts in FIG. 7D are DAPI stains.

Figure 8A:
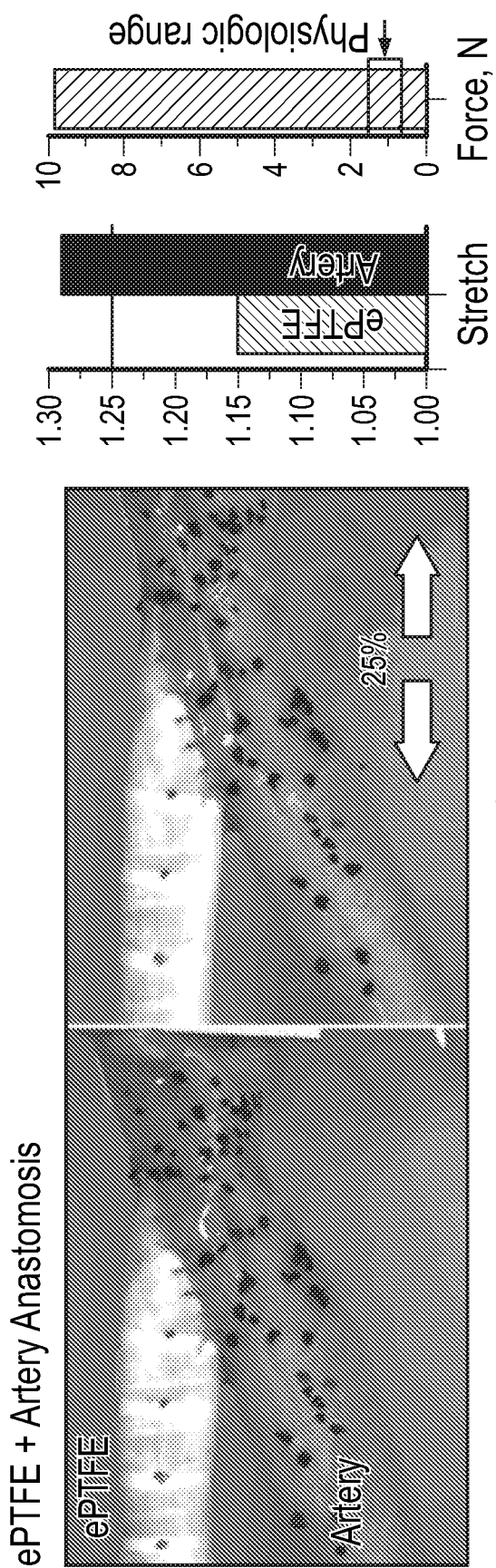
FIG. 8 shows images and graphs illustrating the amount of axial force required to stretch an ePTFE bypass graft (top panel) and one particular embodiment of the NEB bypass graft (lower panel) anastomosed to an 81-year-old human FPA.
Figure 8B:
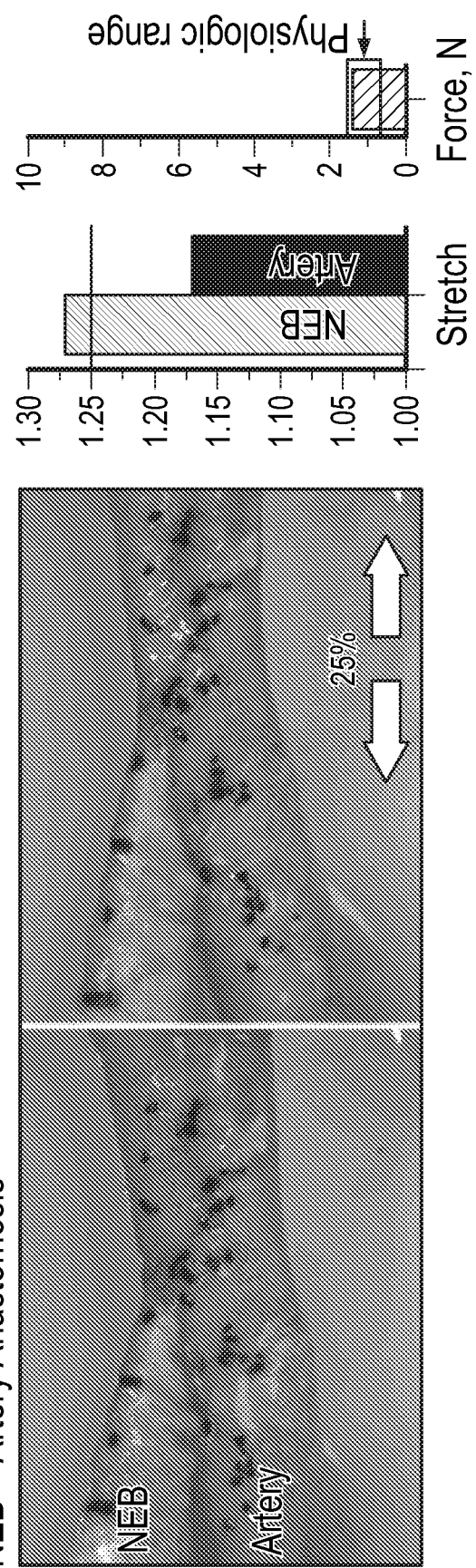

The inventors insured that the nanofibrillar graft material exhibits sufficient permeability, suture retention, and durability. To ensure that the nanofibrillar fabric is suitable for surgical implantation it was tested for permeability, suture retention, and durability according to ANSFAAMI/ISO 7198 standard for cardiovascular implants. Water permeability was assessed on a 1 $cm^2$ circular cross-section of material at 200 mmHg pressure, and results expressed as volume (mL) of water flowing through the 1 $cm^2$ area of graft per minute are presented in FIG. 7A. These results demonstrate that no pre-clotting is required for the nanofibrillar fabric. Mechanical tests demonstrate that nanofibrillar material possesses excellent suture retention properties (2.1N, FIG. 8B), and is both stronger (5.6 MPa) and tougher than human FPA in the circumferential (0.75±0.3 MPa) and longitudinal (0.83±0.4 MPa) directions (FIG. 8C).

Cell viability studies were also performed. Since electro-spinning uses organic solvents that may be toxic to cells, the inventors quantified the amount of residual solvent with thermogravimetric analysis. The data demonstrated that the nanofibrillar material contains <0.1% of the residual solvent immediately after manufacturing, and none can be detected 3 days after manufacturing. Multiple cell culture studies done on the nanofibrillar material demonstrate that primary porcine vSMCs favor the nanofibrillar material versus ePTFE, demonstrating improved material coverage, penetration, and viability seven days in culture (FIG. 7D).

With regard to kink resistance, many currently used ePTFE grafts are reinforced with rings to avoid external compression by surrounding tissue and kinking during limb flexion. This seems particularly important because ePTFE grafts cannot accommodate LPS, and when non-reinforced grafts are longitudinally compressed, they develop kinks that can obstruct blood flow. However, even reinforced ePTFE grafts can develop adverse bending and tortuosity in the flexed limb posture that may significantly alter hemodynamics, and clinical data are conflicting regarding the utility of external graft support. While LPS and the associated tension in the EBG/NEB grafts would avoid kinking in the flexed limb posture, radial pinching induced by surrounding tissues may still compress the lumen and can contribute to obstruction and adverse hemodynamics. To reduce these effects, the inventors developed kink-resistant reinforcements for the EBG/NEB grafts.

The first type of reinforcement uses a thin Nitinol wire stent (FIG. 4, left panel), while the second type uses a polyethylene terephthalate ("PET") spiral that is incorporated into the wall of the EBG/NEB graft during manufacturing (FIG. 4, right panel). Both methods offer higher resistance to radial compression but differ in their interactions with the nanofibrillar fabric. Other materials and types of reinforcement elements can be used.

Regarding anastomotic tension, creating a tension-free anastomosis is a basic principle of cardiovascular surgery. However, animal experiments have demonstrated that a natural amount of tension is not only beneficial, but is required for normal healing, while reduced axial tension is associated with increased cell proliferation and matrix accumulation.

Referring to FIG. 8, the inventors performed a preliminary analysis to determine the amount of axial force required to stretch the ePTFE (top panel) and an example EBG/NEB (lower panel) bypass graft anastomosed to an 81-year-old human FPA. Since the FPA foreshortens 25% during limb flexion, the graft needs to be pre-stretched at least 25% to counteract this deformation and avoid tortuosity in the flexed limb posture. The inventors applied 1.25 axial stretch to the ePTFE/FPA anastomosis, which resulted in 10N of axial force that is more than 5-fold larger than the FPA physiologic axial force (see FIG. 5, right panel) subjecting the anastomosis to significant tension and the risk of disruption. In addition, since stiff ePTFE could not stretch 25%, the adjacent artery had to compensate by overstretching. In contrast, the same amount of axial stretch applied to the NEB/FPA composite resulted in physiologic axial force of 1.5N and physiologic FPA stretch of 17% (see FIG. 5, middle panel), while the NEB stretched 27%. These data corroborate common surgical practice of not subjecting conventional ePTFE bypass grafts to tension, and demonstrate the ability of the EBG/NEB grafts to avoid high tension at the anastomoses while maintaining normal physiologic axial force and LPS typical for human FPAs.

Ringed ePTFE grafts produce large compressive forces at the anastomosis during limb flexion even when not stretched during implantation. Since lower extremity ePTFE grafts are typically implanted without imposing axial tension with the leg in the straight limb posture, they are reinforced with rings to avoid kinking of the graft during limb flexion. While effective for reducing kinks, ring reinforcements may cause significant compressive stress at the graft/artery anastomoses which may contribute to intimal hyperplasia and graft failure. The inventors' bench-top experiments with supported ePTFE grafts demonstrated that a 25% axial compression typical for human FPAs in the flexed limb posture produces 2.1N of compressive axial force, and further compression results in exponentially higher force values reaching greater than 5N at just 30% compression. Such compression is not uncommon in human FPAs that can foreshorten up to 39% in the flexed limb posture. In terms of absolute values, this compressive force is significantly higher than the physiologic axial force that the FPA experiences in vivo due to LPS (see FIG. 5, right panel). In other words, while common surgical practice precludes subjecting the ePTFE graft to any axial stretch to avoid stresses at the anastomosis, these stresses still occur in the flexed limb posture due to axial compression of the ePTFE graft. Furthermore, these anastomotic stresses are highest when the graft is in the bent limb posture and is more tortuous, thereby experiencing the worst hemodynamics, which may further exacerbate the chances of ePTFE graft failure. The ability of the EBG/NEB grafts to accommodate LPS will result in physiologic axial stresses in the straight limb posture when hemodynamics are most optimal, and will reduce anastomotic stresses in the flexed limb when the hemodynamics are most challenging.

Together, inventors demonstrate the innovative ability to manufacture a tunable, biocompatible, and biomimetic EBG/NEB capable of generating physiologic LPS. Additional details below will describe fine-tuning of one example manufacturing process that can be used to produce long reinforced EBG/NEB grafts with mechanical characteristics and LPS of healthy young human FPAs.

Figure 9:
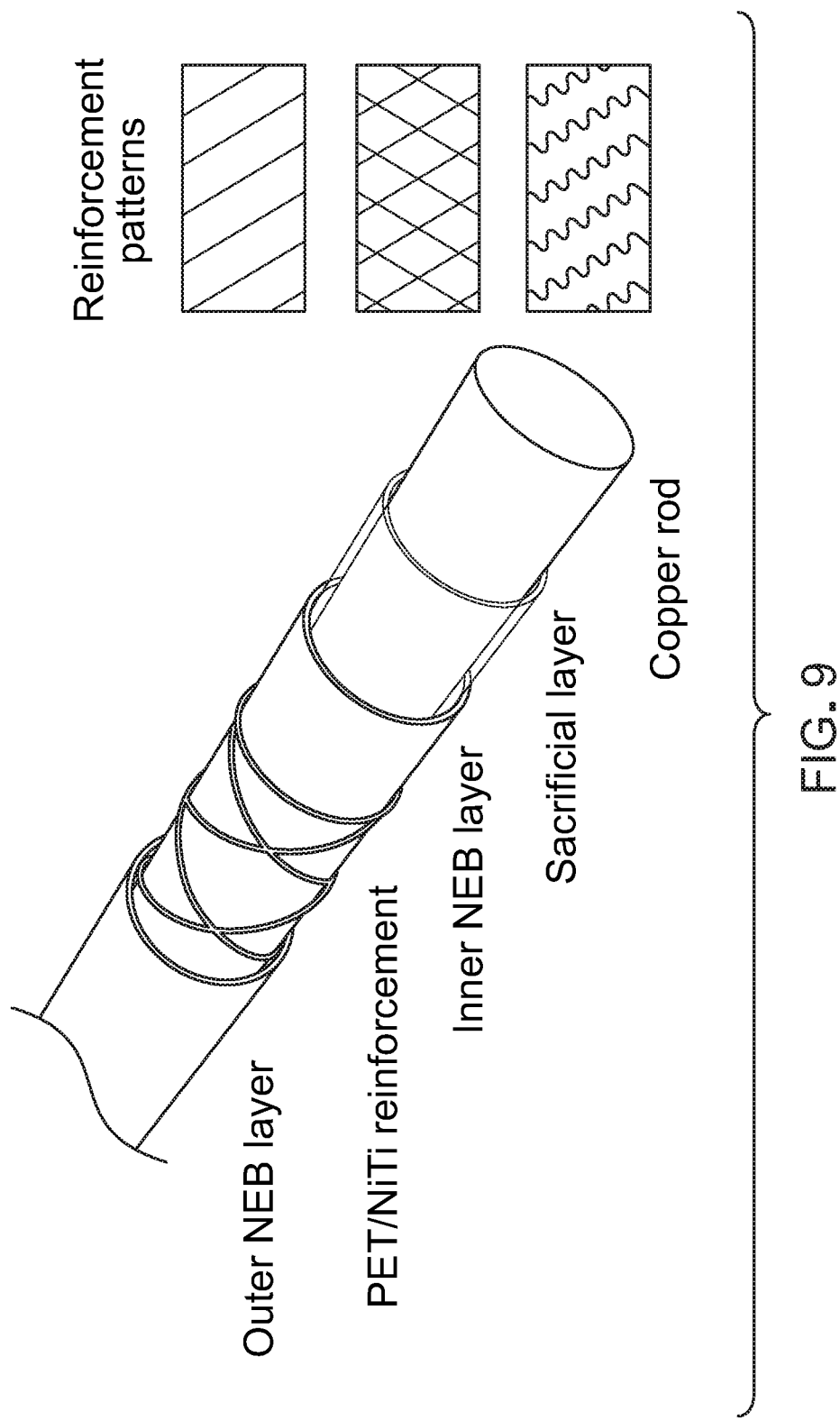
FIG. 9 depicts an example bypass graft construct made using one particular manufacturing technique.

In one particular embodiment, and referring to FIG. 9, an exemplary non-limiting EBG/NEB manufacturing process is demonstrated as using a conductive copper rod, an inner sacrificial layer to facilitate long graft removal, and one or more PET/Nitinol reinforcement members sandwiched between the inner and outer EBG/NEB layers. The panels on the right demonstrate different reinforcement patterns.

In one particular embodiment, tubular EBG/NEB grafts capable of accommodating LPS can be manufactured by electrospinning blends of biocompatible polyether-based urethanes in different proportions on a rotating mandrel. Manufacturing occurs in four steps (see FIG. 9). First, a sacrificial layer is deposited on a conductive copper rod mandrel to facilitate removal of long EBG/NEB grafts from the mandrel. This layer can be made of either electrospun water-soluble biocompatible poly(vinyl acetate), or a flat conductive wire strip tightly coiled on the copper rod. Both methods were explored and allowed easy removal of long grafts from the mandrel without damaging the graft.

Second, the inner EBG/NEB layer is electrospun on top of the sacrificial layer, and a reinforcing framework made either of a stiffer biocompatible polymer such as PET, or a Nitinol alloy will be deposited on top of the inner EBG/NEB layer (see FIG. 4).

Third, reinforcement element(s) is/are added to help prevent buckling and kinking of the EBG/NEB grafts when implanted. PET reinforcement can be patterned using a solution in a syringe mounted on a linear positioner, while the Nitinol reinforcement can be wound. Different patterns of reinforcement (FIG. 9, right panels) can be used to provide kink resistance while also preserving physiologic circumferential stretches and axial force (see FIG. 5).

Fourth, the outer EBG/NEB layer is electrospun on top of the reinforcement element(s) until it is completely incorporated within the nanofibrillar membrane to the desired wall thickness (see FIG. 4). In some embodiments, the reinforcement element(s) can be attached on the outer wall of the graft.

By adjusting electrospinning process parameters the inventors can control the structure and mechanical properties of the EBG/NEB grafts. Alterations in polymer blend ratios allow control of fiber undulation to produce non-linearity (see FIG. 6). Varying the total solution feed volume can be used to control fabric thickness (200-600 µm), and therefore, the overall stiffness of the material. The anisotropy that allows FPAs to accommodate large LPS can be achieved by altering the rotation speed of the mandrel collector. Using these process parameters, combined with the inventors' computational model of FPA limb flexion, EBG/NEB grafts were manufactured that have the non-linear circumferential and longitudinal elastic compliance of healthy human FPAs. These characteristics help create optimal anastomotic tension with physiologic axial force (see FIG. 5) when longitudinally pre-stretched, and achieve optimized hemodynamics due to lack of tortuosity and kinking in the flexed limb posture.

All grafts underwent quality control inspection to ensure consistently reproducible results. The structural composition of the resulting EBG/NEB grafts were assessed with optical and electron microscopy, and mechanical properties were determined with biaxial testing. The inventors also performed permeability, suture retention, and strength testing of the grafts in accordance with ANSI/AAMI/ISO 7198, ISO 25539-1:2017, and ISO 25539-2:2012 standards for cardiovascular implants to ensure their adequate performance. Tests were performed as described in the preliminary data. The devices were then sterilized with Ethylene Oxide, and cell viability studies will be performed to ensure biocompatibility. Cell seeding was performed using primary human and porcine vSMCs at 100,000 cells/cm² seeding density. Grafts were incubated for seven days and evaluated using DAPI and TUNEL stains for cell counts and viability.

The inventors manufactured multiple EBG/NEB graft prototypes (e.g., see FIG. 4) using the processes described above. One potential problem associated with pre-stretching the EBG/NEB grafts might be excessive anastomotic tension that could exceed physiologic levels when attempting to meet other performance requirements, such as circumferential compliance. In such a case the EBG/NEB grafts can be modified by including petals at or close to the graft ends or along the entire length of the graft that can be attached to adjacent diseased bypassed FPA segments to help offload the anastomoses and tune in the required amount of tension. Importantly, this will allow different tunable amounts of tension in different segments of the graft, i.e., less tension at the anastomotic ends, and more tension in the middle of the graft. The inventors' studies in a human cadaver model demonstrated that this approach is feasible.

Figure 10:
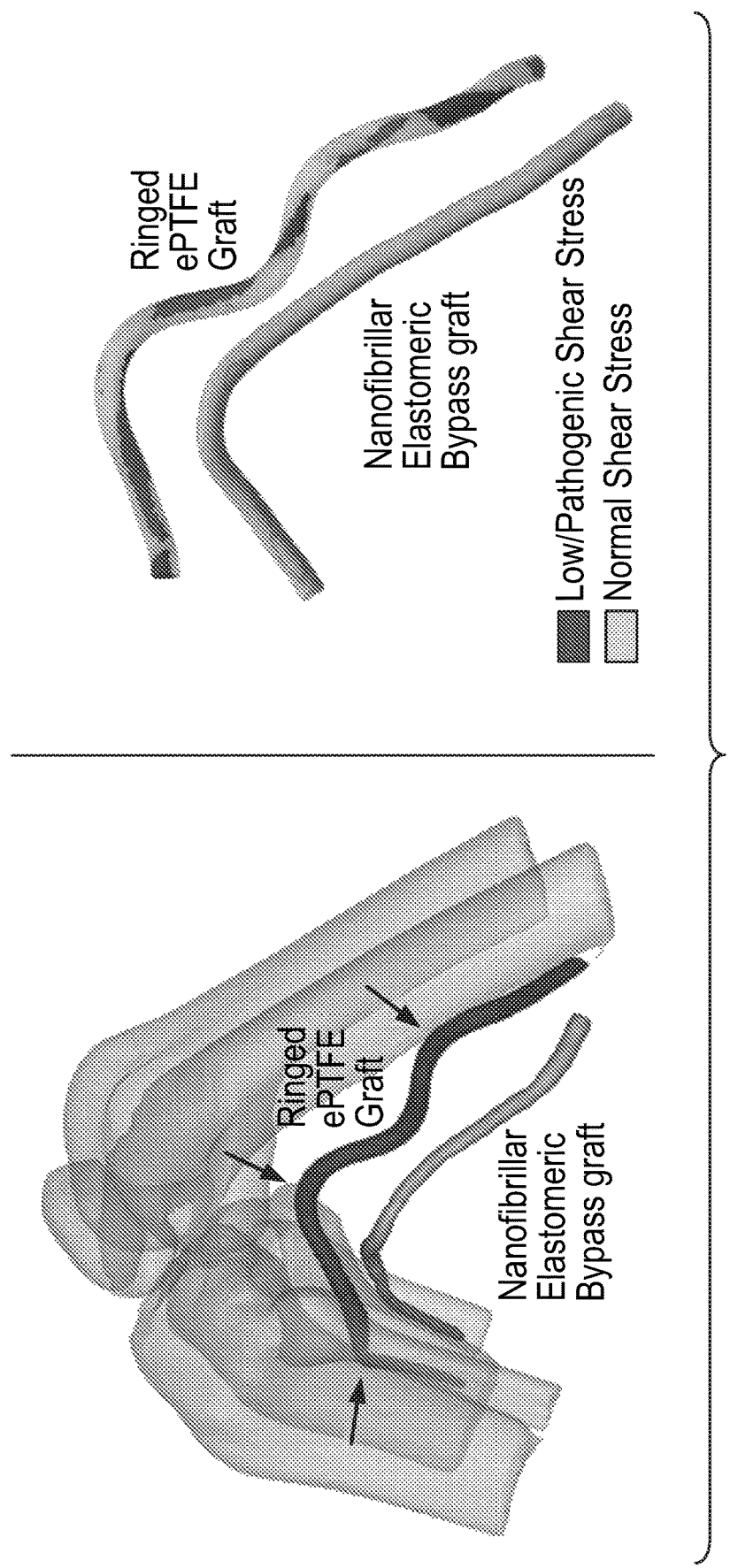
FIG. 10, in the left panel, shows a longitudinally pre-stretched NEB graft (lower) demonstrating minimal bending and no kinking during limb flexion in a perfused human cadaver model as opposed to a standard supported ePTFE graft (upper) that cannot be pre-stretched. The right panel shows an NEB graft that demonstrates more normal hemodynamics in the flexed limb while multiple low shear stress areas are present in the ePTFE graft.

Referring to FIG. 10, the middle panel shows a longitudinally pre-stretched EBG/NEB graft (lower, green) demonstrating minimal bending and no kinking during limb flexion in a perfused human cadaver model as opposed to a standard supported ePTFE graft (upper, blue) that cannot be pre-stretched. The right panel shows computational results of an EBG/NEB graft that demonstrates more normal hemodynamics in the flexed limb while multiple low shear stress areas are present in the ePTFE graft.

EBG/NEB grafts demonstrate superior hemodynamic characteristics in the flexed limb compared with supported ePTFE grafts. While support rings of the ePTFE grafts prevent them from developing acute kinks in the flexed limb posture, the appreciable increased tortuosity of the graft results in adverse graft hemodynamics and multiple zones of slow flow and low shear stress (FIG. 10, right panel).

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable sub-combination. Moreover, although features may be described above as acting in certain combinations and even initially claimed as such, one or more features from a claimed combination may in some examples be excised from the combination, and the claimed combination may be directed to a sub-combination or variation of a sub-combination.

A number of embodiments have been described. Nevertheless, it will be understood that various modifications may be made without departing from the spirit and scope of the disclosure. Accordingly, other embodiments are within the scope of the following claims.

What is claimed is:

1. A vascular bypass graft, comprising:
   an elongate tubular graft made of an elastomeric material that comprises a network of nanofibers arranged to cause the tubular graft to exhibit non-linear elastic compliance in response to increasing longitudinal tensile loads;
   a first pre-stretch regulator coupled to a first end portion of the tubular graft and a second pre-stretch regulator coupled to a second end portion of the tubular graft; and
   one or more wings extending laterally from the tubular graft.

2. The vascular bypass graft of claim 1, wherein the elastomeric material comprises nanofibrillar elastomeric material.

3. The vascular bypass graft of claim 1, wherein the network of nanofibers is arranged to cause the tubular graft to exhibit anisotropic properties.

4. The vascular bypass graft of claim 3, wherein the anisotropic properties include a greater longitudinal compliance than radial compliance.

5. The vascular bypass graft of claim 1, further comprising one or more reinforcing elements disposed between an inner layer of the elastomeric material and an outer layer of the elastomeric material.

6. The vascular bypass graft of claim 5, wherein the one or more reinforcing elements comprises an undulating wire spirally wrapped between the inner and outer layers of the elastomeric material.

7. The vascular bypass graft of claim 5, wherein the one or more reinforcing elements comprises an elongate element spirally wrapped between the inner and outer layers of the elastomeric material.

8. The vascular bypass graft of claim 5, wherein the one or more reinforcing elements comprises an elongate polyethylene terephthalate element spirally wrapped between the inner and outer layers of the elastomeric material.

9. The vascular bypass graft of claim 1, wherein the first and second pre-stretch regulators comprise tethers.

10. A method of implanting a blood vessel bypass graft, the method comprising:
    creating a first anastomosis between a vascular bypass graft and a native blood vessel; and
    creating a second anastomosis between the vascular bypass graft and the native blood vessel,
    longitudinally pre-stretching the vascular bypass graft so that the vascular bypass graft is in tension between the first and second anastomoses,
    wherein the vascular bypass graft comprises an elastomeric material made of a network of nanofibers arranged to cause the vascular bypass graft to exhibit non-linear elastic compliance in response to increasing longitudinal tensile loads.

11. The method of claim 10, further comprising:
    attaching to the native blood vessel a first pre-stretch regulator that is coupled to a first end portion of the vascular bypass graft; and
    attaching to the native blood vessel a second pre-stretch regulator that is coupled to a second end portion of the vascular bypass graft.

12. The method of claim 10, further comprising:
    attaching to the native blood vessel one or more wings that extend laterally from the vascular bypass graft.

13. The method of claim 10, wherein: creating the first anastomosis between the vascular bypass graft and the native blood vessel comprises creating the first anastomosis between the vascular bypass graft and a femoropopliteal artery; and
    creating the second anastomosis between the vascular bypass graft and the native blood vessel comprises creating the second anastomosis between the vascular bypass graft and the femoropopliteal artery.

14. A method of making a prosthetic blood vessel bypass graft, the method comprising:

depositing a first layer of elastomeric material onto a rotating mandrel, wherein the elastomeric material comprises polyether-based urethane;

positioning one or more reinforcing framework members on the first layer; and depositing a second layer of the elastomeric material onto the first layer and the one or more reinforcing framework members while the mandrel is rotating, wherein the blood vessel bypass graft is configured to be longitudinally pre-stretched so that the blood vessel bypass graft is in tension between a first anastomosis and second anastomosis following implantation of the blood vessel bypass graft.

15. The method of claim 14, wherein the method results in the prosthetic blood vessel bypass graft exhibiting non-linear elastic compliance in response to increasing longitudinal tensile loads.

16. The method of claim 14, wherein at least one of the depositing the first layer of the elastomeric material or the depositing the second layer of the elastomeric material comprises electrospinning, and wherein the method further comprises controlling fiber undulation of the elastomeric material to attain a desired level of non-linear elastic compliance.

17. The method of claim 14, wherein the method results in the prosthetic blood vessel bypass graft exhibiting anisotropic properties comprising a greater longitudinal compliance than radial compliance.

* * * * *

UNITED STATES PATENT AND TRADEMARK OFFICE
CERTIFICATE OF CORRECTION

PATENT NO. : 12,303,376 B2
APPLICATION NO. : 17/282564
DATED : May 20, 2025
INVENTOR(S) : Jason N. MacTaggart et al.

It is certified that error appears in the above-identified patent and that said Letters Patent is hereby corrected as shown below:

In the Specification

In Column 1, Line 11 (Approx.), delete "hereby, which is" and insert -- hereby --.

In Column 1, Line 12 (Approx.), delete "in its entirety-herein" and insert -- herein --.

Signed and Sealed this
First Day of July, 2025

Coke Morgan Stewart
*Acting Director of the United States Patent and Trademark Office*